United States Patent
Feng

(10) Patent No.: US 11,945,946 B2
(45) Date of Patent: Apr. 2, 2024

(54) POLYUREA AND POLY(BETA-AMINO ESTER) CAPSULES WITH ENHANCED DEGRADABILITY

(71) Applicant: Encapsys, LLC, Appleton, WI (US)

(72) Inventor: Linsheng Feng, Menasha, WI (US)

(73) Assignee: ENCAPSYS, LLC, Appleton, WI (US)

( * ) Notice: Subject to any disclaimer, the term of this patent is extended or adjusted under 35 U.S.C. 154(b) by 38 days.

(21) Appl. No.: 17/473,180

(22) Filed: Sep. 13, 2021

(65) Prior Publication Data

US 2022/0081560 A1  Mar. 17, 2022

Related U.S. Application Data

(60) Provisional application No. 63/077,914, filed on Sep. 14, 2020.

(51) Int. Cl.

| | | |
|---|---|---|
| C08L 75/02 | (2006.01) | |
| A01N 25/28 | (2006.01) | |
| A01N 43/40 | (2006.01) | |
| A61K 8/11 | (2006.01) | |
| A61K 8/81 | (2006.01) | |
| A61K 8/84 | (2006.01) | |
| A61K 8/85 | (2006.01) | |
| A61Q 13/00 | (2006.01) | |
| B01J 13/16 | (2006.01) | |
| C08L 29/04 | (2006.01) | |
| C08L 35/02 | (2006.01) | |
| C08L 67/02 | (2006.01) | |
| C08L 79/02 | (2006.01) | |
| C11D 3/37 | (2006.01) | |
| C11D 3/50 | (2006.01) | |

(52) U.S. Cl.
CPC .............. *C08L 75/02* (2013.01); *A01N 25/28* (2013.01); *A01N 43/40* (2013.01); *A61K 8/11* (2013.01); *A61K 8/8129* (2013.01); *A61K 8/8152* (2013.01); *A61K 8/84* (2013.01); *A61K 8/85* (2013.01); *A61Q 13/00* (2013.01); *B01J 13/16* (2013.01); *C08L 29/04* (2013.01); *C08L 35/02* (2013.01); *C08L 67/02* (2013.01); *C08L 79/02* (2013.01); *C11D 3/3726* (2013.01); *C11D 3/505* (2013.01); *A61K 2800/412* (2013.01); *A61K 2800/54* (2013.01); *A61K 2800/56* (2013.01); *C08L 2201/52* (2013.01); *C08L 2207/53* (2013.01)

(58) Field of Classification Search
CPC .......... C08L 75/02; C08L 29/04; C08L 35/02; C08L 67/02; C08L 79/02; C08L 2201/52; C08L 2207/53; A01N 25/28; A01N 43/40; A61K 8/11; A61K 8/8129; A61K 8/8152; A61K 8/84; A61K 8/85; A61K 2800/412; A61K 2800/54; A61K 2800/56; A61Q 13/00; B01J 13/16; C11D 3/3726; C11D 3/505

See application file for complete search history.

(56) References Cited

U.S. PATENT DOCUMENTS

| | | | |
|---|---|---|---|
| 7,427,394 B2 | 9/2008 | Anderson et al. | |
| 8,808,681 B2 | 8/2014 | Anderson et al. | |
| 2017/0113200 A1* | 4/2017 | Zhang | A61K 9/50 |
| 2017/0216162 A1* | 8/2017 | Feng | B01F 23/00 |
| 2019/0125874 A1 | 5/2019 | Anderson et al. | |

* cited by examiner

*Primary Examiner* — Doan T Phan

(74) *Attorney, Agent, or Firm* — Muncy, Geissler, Olds & Lowe, P.C.

(57) ABSTRACT

Microcapsules encapsulating oily core materials have a shell material of hybrid polyurea and poly(beta-amino esters) (PU/PBAE). The microcapsules may have a single shell of hybrid PU/PBAE, dual shells including hybrid PU/PBAE in an inner shell and PBAE in an outer shell crosslinked and deposited to the inner shell, or multiple shells including PU in an inner shell, hybrid PU/PBAE in a transitioning shell, and PBAE in an outer shell. Formation of the microcapsules includes polymerization between multifunctional amine and multifunctional acrylate to produce a water soluble PBAE; polymerization between polyisocyanate in oil phase and multifunctional amine in aqueous solution to produce PU microcapsule, polymerization between polyisocyanate and the amine moiety of PBAE prepolymer to produce hybrid PU/PBAE microcapsule wall; and polymerization between multifunctional acrylate and primary or secondary amine moiety of the PBAE prepolymer to form a PBAE outer shell.

31 Claims, 2 Drawing Sheets

POLYUREA AND POLY(BETA-AMINO ESTER) CAPSULES WITH ENHANCED DEGRADABILITY

CROSS REFERENCE TO RELATED APPLICATIONS

This application claims priority of U.S. Provisional Application No. 63/077,914 filed on Sep. 14, 2020 under 35 U.S.C. § 119(e), the entire content of which is hereby incorporated by reference.

FIELD OF DISCLOSURE

The present invention relates to encapsulation compositions for encapsulating active material and processes for making such encapsulation compositions, and in particular to an encapsulation composition including the polymeric shell of the capsules comprising a hybrid polymer of polyurea and poly(beta-amino esters) (PU/PBAE) and encapsulating oil phase active material.

BACKGROUND OF THE INVENTION

Microencapsulation is a process of building a functional barrier between the core material and the surrounding material to avoid chemical and physical reactions and to maintain the biological, functional, and physicochemical properties of core material. Microencapsulating particulate materials are of interest where there is a need to deliver, apply, or release an active material including, for example, a fragrance, flavor, and pesticide, to a target area in a time-delayed or controlled manner.

In view of the many uses for microencapsulation in many diverse fields, it is desirable to provide a microencapsulation composition with improved biodegradability and encapsulation performance at the same time, which would allow for protection against unwanted degradation, targeting specific and controlled release of the active substance, facilitating increased efficacy and availability, and removal from the body via normal metabolic pathways.

Poly(beta-amino esters) (PBAE) polymers are widely used in biomedical fields due to their biocompatibility and biodegradability. For example, U.S. Pat. No. 7,427,394 B2 relates to PBAE prepared from the conjugate addition of bis(secondary amines) or primary amines to a bis(acrylate ester). Methods of preparing these polymers from commercially available starting materials are also provided in this disclosure. The patentees suggest that the PBAE polymers may also be used to encapsulate other agents to be delivered. They are particularly useful in delivering labile agents given their ability to buffer the pH of their surroundings.

U.S. Pat. No. 8,808,681 B2 relates to acrylate-terminated PBAE cross-linked to form materials useful in the medical as well as non-medical field. The resulting materials due to the hydrolysable ester bond in the polymer backbone are biodegradable under physiological conditions. These cross-linked materials are particular useful as drug delivery vehicles, tissue engineering scaffolds, and in fabricating microdevices. The materials may also be used as plastics, coating, adhesives, inks, etc. The cross-linked materials exhibit a wide range of degradation times, mass loss profiles, and mechanical properties. Therefore, the properties of the material may be tuned for the desired use. The high-throughput approach to prepare a library of cross-linked PBAE allows for the rapid screening and design of degradable polymers for a variety of applications.

U.S. Patent Application Publication 2019/0125874 relates to PBAE useful as vehicles for the delivery of therapeutic agents, such as nucleic acids. The disclosed polymers form stable compositions, and are suitable for the delivery of therapeutic agents via nebulization.

It would be desirable to have an encapsulation composition with both enhanced degradability and encapsulation performance at the same time.

SUMMARY OF THE INVENTION

The objective of the present invention is to manufacture a PU/PBAE microcapsule. The microcapsule can have any of a single shell, double shell, or multiple shell structure with improved degradability, encapsulation performance and customized properties.

Exemplary embodiments of the invention are directed to a polyurea and poly(beta-amino esters) (PU/PBAE) microcapsule, including a core material; and a shell having a composition including PU, PBAE, and hybrid PU/PBAE.

Exemplary embodiments of the invention are also directed to a PU/PBAE microcapsule, wherein the shell is derived from i) 5% to 90% of a preformed PBAE prepolymer or a reaction product of a first multifunctional acrylate and a multifunctional amine, ii) 0.1% to 90% of a polyisocyanate, and iii) 0% to 90% of a second multifunctional acrylate, by weight of the microcapsule shell.

Exemplary embodiments of the invention are also directed to a PU/PBAE microcapsule, wherein the preformed PBAE prepolymer is derived from the first multifunctional acrylate and the multifunctional amine, wherein a molar ratio of the first multifunctional acrylate to the multifunctional amine is in a range between 100/1-1/100, preferably between 10/1-1/10, more preferably between 2/1-1/2.

Exemplary embodiments of the invention are also directed to a PU/PBAE microcapsule, wherein a molar ratio of the polyisocyanate to the multifunctional amine is 1/100-1/1.

Exemplary embodiments of the invention are also directed to a PU/PBAE microcapsule, wherein the shell is derived from i) 5% to 90% of a multifunctional amine, ii) 0.1% to 90% of a polyisocyanate, and iii) 5% to 90% of a multifunctional acrylate, by weight of the microcapsule shell.

Exemplary embodiments of the invention are also directed to a PU/PBAE microcapsule, wherein the shell includes PU, PBAE, and/or hybrid PU/PBAE and has a single shell structure.

Exemplary embodiments of the invention are directed to a PU/PBAE microcapsule, wherein the shell has an inner surface and an outer surface, or a dual shell structure including an inner shell and an outer shell, a composition of the dual shell structure includes PU and hybrid PU/PBAE in the inner shell or the inner surface and PBAE in the outer shell or the outer surface, wherein the composition of the outer shell or the outer surface crosslinks or deposits to the composition of the inner shell or the inner surface.

Exemplary embodiments of the invention are directed to a PU/PBAE microcapsule, wherein the shell has a multi-shell structure, a composition of the multi-shell structure includes PU in an inner shell, hybrid PU/PBAE in a transitional shell, and PBAE in an outer shell, the composition of each shell crosslinks or deposits to the composition of an adjacent shell.

Exemplary embodiments of the invention are directed to a PU/PBAE microcapsule, wherein a median particle size of the PU/PBAE microcapsule is 3-100 μm.

Exemplary embodiments of the invention are directed to a PU/PBAE microcapsule, wherein a zeta potential of the PU/PBAE microcapsule is −100 mV-+200 mV at pH 3 and −200 mV-+100 mV at pH 10.

Exemplary embodiments of the invention are directed to a method of producing a PU/PBAE microcapsule, including:

providing a first aqueous solution comprising an emulsifier and water;

providing a second aqueous solution comprising a multifunctional amine, a first multifunctional acrylate and water, and mixing the second aqueous solution at a first temperature for a first period of time;

adding the first aqueous solution into the second aqueous solution under mixing to obtain a mixture of the first aqueous solution and the second aqueous solution;

providing an oil phase comprising the core material and a polyisocyanate;

adding the oil phase into the mixture of the first aqueous solution and the second aqueous solution, applying high shear agitation at a second temperature until a target particle size is reached to obtain an emulsion;

providing a third aqueous solution comprising a second multifunctional acrylate, adding the third aqueous solution into the emulsion under mixing; and increasing a temperature to a third temperature in a second period of time and holding the temperature at the third temperature for a third period of time under mixing.

Exemplary embodiments of the invention are directed to a method of producing a PU/PBAE microcapsule, wherein the second aqueous solution does not include a multifunctional acrylate.

Exemplary embodiments of the invention are directed to a method of producing a PU/PBAE microcapsule, wherein the third aqueous solution is not provided and is not added into the emulsion containing the first aqueous solution, the second aqueous solution and the oil phase.

Exemplary embodiments of the invention are directed to a method of producing a PU/PBAE microcapsule, wherein the multifunctional amine is diethylenetriamine, ethylenediamine, or polyethylenimine, the first and the second multifunctional acrylate is diethylene glycol diacrylate, trifunctional trimethylolpropane triacrylate, ethoxylated trimethylolpropane triacrylate independently or a combination therefore indepently, the polyisocyanate is dicyclohexylmethane diisocyanate (Desmodur® W), hexamethylene diisocyanate uretdione (Desmodur® N3400), or xylyene diisocyanate (XDI) based aliphatic polyisocyanate adduct prepolymer (TakeNate® D110N).

Exemplary embodiments of the invention are directed to a method of producing a PU/PBAE microcapsule, wherein the first temperature is 25-70° C., the second temperature is 5-55° C., the third temperature is 50-95° C., the first period of time is 10-360 mins, the second period of time is 30-120 mins, and the third period of time is 2-24 hours.

Exemplary embodiments of the invention are directed to a method of producing the PU/PBAE microcapsule, including:

providing a first aqueous solution comprising an emulsifier and water;

providing a second aqueous solution comprising a multifunctional amine, a first multifunctional acrylate and water, and mixing the second aqueous solution at a first temperature for a first period of time;

providing an oil phase comprising the core material and a polyisocyanate;

adding the oil phase into the first aqueous solution, applying high shear agitation at a second temperature until a target particle size is reached, and then switching to mix to obtain a first emulsion;

adding the second aqueous solution into the first emulsion under mixing to obtain a second emulsion;

providing a third aqueous solution comprising a second multifunctional acrylate, and adding the third aqueous solution into the second emulsion under mixing; and increasing a temperature to a third temperature in a second period of time and hold the temperature at the third temperature for a third period of time under mixing.

Exemplary embodiments of the invention are directed to a method of producing a PU/PBAE microcapsule, wherein the second aqueous solution does not include a multifunctional acrylate.

Exemplary embodiments of the invention are directed to a method of producing a PU/PBAE microcapsule, wherein the third aqueous solution is not provided and is not added into the emulsion containing the first aqueous solution, the second aqueous solution and the oil phase.

Exemplary embodiments of the invention are directed to a method of producing a PU/PBAE microcapsule, wherein the multifunctional amine is diethylenetriamine, ethylenediamine, or polyethylenimine, the first and the second multifunctional acrylate is diethylene glycol diacrylate, trifunctional trimethylolpropane triacrylate, ethoxylated trimethylolpropane triacrylate, or a combination thereof independently, the polyisocyanate is dicyclohexylmethane diisocyanate (Desmodur® W), hexamethylene diisocyanate uretdione (Desmodur® N3400), or xylyene diisocyanate (XDI) based aliphatic polyisocyanate adduct prepolymer (TakeNate® D110N).

Exemplary embodiments of the invention are directed to a method of producing a PU/PBAE microcapsule, wherein the first temperature is 25-70° C., the second temperature is 5-55° C., the third temperature is 50-95° C., the first period of time is 10-360 mins, the second period of time is 30-120 mins, and the third period of time is 2-24 hours.

Exemplary embodiments of the invention are directed to an article of manufacture incorporating the PU/PBAE microcapsules.

Exemplary embodiments of the invention are directed to the article of manufacture incorporating the PU/PBAE microcapsules, wherein the article is a soap, a surface cleaner, a laundry detergent, a fabric softener, a shampoo, a textile, a paper towel, an adhesive, a wipe, a diaper, a feminine hygiene product, a facial tissue, a pharmaceutical, a napkin, a deodorant, a heat sink, a foam, a pillow, a mattress, bedding, a cushion, a cosmetic, a medical device, packaging, an agricultural product, a cooling fluid, a wallboard, or an insulation.

The above as well as additional objectives, features, and advantages of the present invention are detailed in the description below, as well as in the drawings.

BRIEF DESCRIPTION OF THE DRAWINGS

The accompanying drawings are presented to aid in the description of embodiments of the invention and are provided solely for illustration of the embodiments and not limitation thereof.

DETAILED DESCRIPTION OF THE INVENTION

Figure 1:
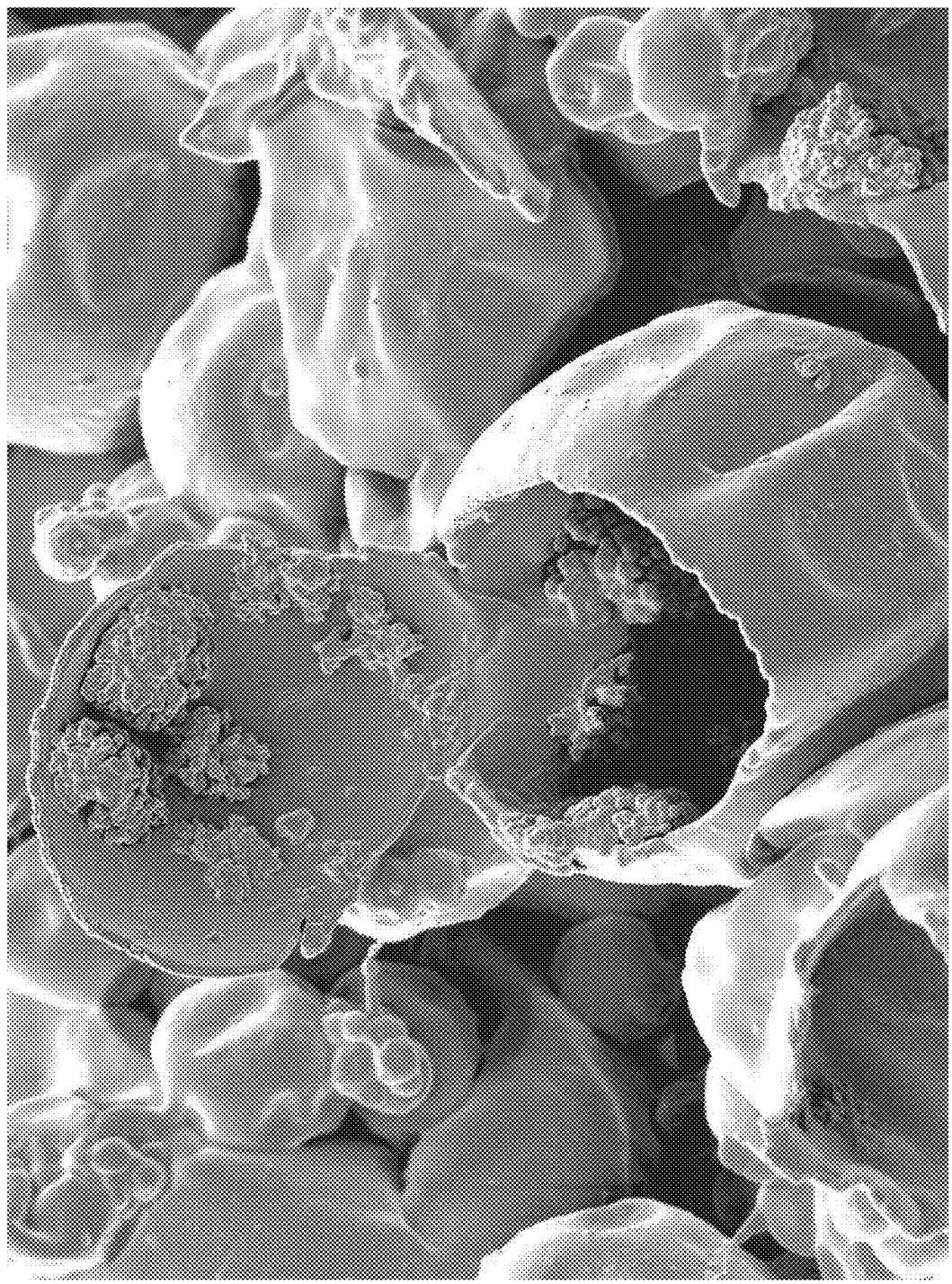
FIG. 1 is a scanning electron microscope (SEM) image of the microcapsules of Example 14 of the present invention.

The present invention is based on the discovery that encapsulation using PBAE prepolymer, produced by polymerization reaction of multifunctional amines with multifunctional acrylates, further polymerizing with polyisocyanates can yield microcapsules with improved encapsulation performance and enhanced degradability.

For purposes of the invention, polyisocyanates are understood as encompassing any polyisocyanate having at least two isocyanate groups and comprising an aliphatic or aromatic moiety in the monomer, oligomer or prepolymer. Multifunctional amines herein are to be understood including any monomer, oligomer, or polyamine that has two primary amines groups and one or multiple secondary amines groups. Multifunctional acrylate is to be understood as referring to a compound having at least two acrylate groups and comprising multifunctional acrylate monomer, oligomer and/or prepolymer.

Specifically, a multifunctional amine polymerizes with a multifunctional acrylate to form a PBAE prepolymer. In addition, a polyisocyanate polymerizes with the multifunctional amine to form a PU microcapsule shell or with the primary or secondary amine moiety of PBAE prepolymer to form hybrid PU/PBAE in or on the microcapsule shell. Further, the acrylate moiety of the PBAE and excess multifunctional acrylate if any also compete with polyisocyanate in reaction with the multifunctional amine and the primary and the secondary amine moiety of PBAE. These competing reactions can be advantageously employed to create a PU/PBAE microcapsule including PU, hybrid PU/PBAE and PBAE with a single shell, advantageously dual shells, or multiple shells through the control of the relative amounts of different reactants, the presence or absence of the pre-polymerization step, and the reaction sequence in forming the microcapsules. A unique microcapsule with customized properties is thereby achievable.

In one embodiment, the PU/PBAE microcapsule shell contains 5% to 90% of the preformed PBAE prepolymer or polyamines, 0.1% to 90% of the polyisocyanate, and 0% to 90% of multifunctional acrylate by weight of the microcapsule shell, provided that the sum of the PBAE prepolymer or polyamines, the polyisocyanate, and the multifunctional acrylate is 100%.

The PU/PBAE microcapsule encapsulates an oil phase core material. To encapsulate the oil phase core material, a first aqueous solution is prepared by mixing an emulsifier with water.

Non-limiting examples of emulsifiers include water-soluble salts of alkyl sulfates, alkyl ether sulfates, alkyl isothionates, alkyl carboxylates, alkyl sulfosuccinates, alkyl succinamates, alkyl sulfate salts such as sodium dodecyl sulfate, alkyl sarcosinates, alkyl derivatives of protein hydrolyzates, acyl aspartates, alkyl or alkyl ether or alkylaryl ether phosphate esters, sodium dodecyl sulphate, phospholipids, lecithin, soaps, sodium, potassium or ammonium stearate, oleate, palmitate, alkylarylsulfonic acid salts such as sodium dodecylbenzenesulfonate, sodium dialkylsulfosuccinates, dioctyl sulfosuccinate, sodium dilaurylsulfosuccinate, poly(styrene sulfonate) sodium salt, isobutylene-maleic anhydride copolymer, gum arabic, sodium alginate, carboxymethylcellulose, cellulose sulfate and pectin, poly (styrene sulfonate), isobutylene-maleic anhydride copolymer, carrageenan, sodium alginate, pectic acid, tragacanth gum, almond gum and agar; semi-synthetic polymers such as carboxymethyl cellulose, sulfated cellulose, sulfated methylcellulose, carboxymethyl starch, phosphated starch, lignin sulfonic acid; synthetic polymers such as maleic anhydride copolymers (including hydrolyzates thereof), polyacrylic acid, polymethacrylic acid, acrylic acid butyl acrylate copolymer or crotonic acid homopolymers and copolymers, vinyl benzenesulfonic acid or 2-acrylamido-2-methylpropanesulfonic acid homopolymers and copolymers, and partial amide or partial ester of such polymers and copolymers, carboxy modified polyvinyl alcohol, sulfonic acid-modified polyvinyl alcohol and phosphoric acid-modified polyvinyl alcohol, phosphated or sulfated tristyrylphenol ethoxylates, palmitamidopropyltrimonium chloride (Varisoft PATC™, available from Degussa Evonik, Essen, Germany), distearyl dimonium chloride, cetyltrimethylammonium chloride, quaternary ammonium compounds, fatty amines, aliphatic ammonium halides, alkyldimethylbenzylammonium halides, alkyldimethylethylammonium halides, polyethyleneimine, poly(2-dimethylamino)ethyl methacrylate) methyl chloride quaternary salt, poly(1-vinylpyrrolidone-co-2-dimethylaminoethyl methacrylate), poly(acrylamide-co-diallyldimethylammonium chloride), poly (allylamine), poly[bis(2-chloroethyl) ether-alt-1,3-bis[3-(dimethylamino)propyl]urea] quaternized, and poly (dimethylamine-co-epichlorohydrin-co-ethylenediamine), condensation products of aliphatic amines with alkylene oxide, quaternary ammonium compounds with a long-chain aliphatic radical, e.g. distearyldiammonium chloride, and fatty amines, alkyldimethylbenzylammonium halides, alkyldimethylethylammonium halides, polyalkylene glycol ether, condensation products of alkyl phenols, aliphatic alcohols, fatty acids with alkylene oxide, ethoxylated alkyl phenols, ethoxylated aryl phenols, ethoxylated polyaryl phenols, carboxylic esters solubilized with a polyol, polyvinyl alcohol, polyvinyl acetate, or copolymers of polyvinyl alcohol polyvinyl acetate, polyacrylamide, poly(N-isopropylacrylamide), poly(2-hydroxypropyl methacrylate), poly(-ethyl-2-oxazoline), poly(2-isopropenyl-2-oxazoline-co-methyl methacrylate), poly(methyl vinyl ether), poly(vinyl alcohol-co-ethylene), or cocoamidopropyl betaine.

Emulsifier, if employed, is typically from about 0.1 to 40% by weight, preferably 0.2 to about 15% by weight, more typically 0.5 to 10% by weight, based on the total weight of the formulation.

In one embodiment of the present invention, the emulsifier is polyvinyl alcohol such as Selvol™ Polyvinyl Alcohol 540 (Sekisui Specialty Chemicals America, LLC).

A second aqueous solution containing water soluble PBAE prepolymer is prepared by dissolving a multifunctional amine in water under mixing at a temperature of 25° C.-70° C. Then, a multifunctional acrylate, for example, a bifunctional acrylate, is added into the multifunctional amine solution. A prepolymer is formed by mixing the multifunctional amine and the multifunctional acrylate for a period of time of 10-360 mins at a temperature of 25-70° C. The molar ratio of the multifunctional acrylate and the multifunctional amine is between 100/1-1/100, preferably between 10/1-1/10, more preferably between 2/1-1/2.

During the above descried step, a water soluble or dispersible PBAE prepolymer is produced by the polymerization reaction between the amine group of the multifunctional amine monomer, oligomer, or prepolymer and the acrylate group of a multifunctional acrylate. Generally, the reaction here proceeds by aza-Michael addition to the β-carbon atom of α,β-unsaturated carbonyls of the multifunctional acrylate.

As used herein, reference to the term "acrylate" or "acrylic" is to be understood as referring to the acrylate version of the specified monomer, oligomer and/or prepolymer. For example, multifunctional acrylate, alkyl esters of acrylic acid, and polyacrylate. Each alkyl moiety herein, unless otherwise indicated, can be from $C_1$ to $C_8$, or even from $C_1$ to $C_{24}$. Polyacrylate materials are intended to encompass a broad spectrum of polymeric materials including, for example, polyester polyacrylates, urethane and polyurethane polyacrylates (especially those prepared by the reaction of an hydroxyalkyl acrylate with a polyisocyanate or a urethane polyisocyanate), methyl cyanoacrylate, ethyl cyanoacrylate, diethylene glycol diacrylate, trimethylolpropane triacrylate, ethylene glycol diacrylate, allyl acrylate, glycidyl acrylate, acrylate functional silicones, di-, tri- and tetra ethylene glycol diacrylate, dipropylene glycol diacrylate, polyethylene glycol diacrylate, di(penta methylene glycol) diacrylate, ethylene diacrylate, neopentyl glycol diacrylate, trimethylolpropane triacrylate, ethoxylated bisphenol A diacrylates, bisphenol A diacrylates, diglycerol diacrylate, tetra ethylene glycol dichloroacrylate, 1,3-butanediol diacrylate, neopentyl diacrylate, trimethylolpropane triacrylate, polyethylene glycol diacrylate, dipropylene glycol diacrylate, various multifunctional acrylates, and multifunctional amine acrylates.

Non-limiting examples of multifunctional acrylate monomers, oligomers and prepolymers thereof include ethylene glycol diacrylate, trimethylolpropane triacrylate, trimethylolpropane triacrylate, pentaerythritol tetraacrylate, tricyclodecane dimethanol diacrylate, 1,10 decanediol diacrylate, 1,6 hexanediol diacrylate, 1,9 nonanediol diacrylate, neopentyl glycol diacrylate, di-trimethylolpropane tetraacrylate, dipentaerythritol pentaacrylate, ethoxylated (2) bisphenol A diacrylate, 2,2 bis[4-(acyloyl ethoxy) phenyl]propane, ethoxylated (3) bisphenol A diacrylate, dipropylene glycol diacrylate, ethoxylated (4) bisphenol A diacrylate, ethoxylated (4) bisphenol A diacrylate, 2,2 bis[4-(acyloyl ethoxy) phenyl] propane, pentaerythritol triacrylate, polyethylene glycol 200 diacrylate, ethoxylated (9) trimethylolpropane triacrylate, 2,2 bis[4-(acyloyl ethoxy) phenyl] propane, ethoxylated (30) BPA diacrylate, ethoxylated (15) trimethylolpropane triacrylate, ethoxylated glycerine triacrylate, ethoxylated (20) trimethylolpropane triacrylate, polyethylene glycol 400 diacrylate, polyethylene glycol 600 diacrylate, ethoxylated glycerine triacrylate, ethoxylated pentaerythritol tetraacrylate, polyethylene glycol 1000 diacrylate, polyethylene (200) glycol diacrylate, polyethylene glycol (200) diacrylate, polyethylene glycol (400) diacrylate, polyethylene glycol (600) diacrylate and tris (2-hydroxy ethyl) isocyanurate triacrylate, diethylene glycol diacrylate, ethoxylated (3) trimethylolpropane triacrylate, polypropylene glycol 400 diacrylate, ethoxylated (10) bisphenol A diacrylate, ethoxylated (10) bisphenol A diacrylate, 2,2 bis[4-(acryloyl ethoxy) phenyl] propane, ethoxylated (4) pentaerythritol tetraacrylate, triethylene glycol diacrylate, 2-hydroxyl 1-3 diacryloxy propane, ethoxylated (6) trimethylolpropane triacrylate, ethoxylated propyleneglycol diacrylate, 2,2 bis[4-(acryloyl ethoxy) phenyl] propane and the like, and mixtures of any of the foregoing.

Non-limiting examples of multifunctional amine includes diethylenetriamine, triethylenetetramine, tetraethylenepentamine, pentaethylenehexamine, polyethylenimine or similar amines that have two primary amines and one or multiple secondary amines.

In one embodiment, the molar amount of the acrylate group of the multifunctional acrylate is the same as the molar amount of the primary amine of the multifunctional amine.

An oil phase to be encapsulated as the core material is prepared by mixing the active material with a polyisocyanate such as a diisocyanate. The diisocyanate can be aliphatic or aromatic diisocyanate monomer, oligomer or prepolymer. Non-limiting examples of diisocyanate or polyisocyanate include dicyclohexylmethane diisocyanate (Desmodur® W), hexamethylene diisocyanate uretdione (Desmodur® N3400), xylyene diisocyanate (XDI) based aliphatic polyisocyanate adduct prepolymer (TakeNate® D110N).

Non-limiting examples of useful isocyanates include isocyanate monomers, isocyanate oligomers, isocyanate prepolymers, or dimers or trimers of aliphatic or aromatic isocyanates. All such monomers, prepolymers, oligomers, or dimers or trimers of aliphatic or aromatic isocyanates are intended to be encompassed by the term "polyisocyanate" herein.

The polyisocyanate can be selected from an aliphatic or aromatic monomer, oligomer or prepolymer with two or more isocyanate functional groups. Optimal crosslinking can be achieved with polyisocyanates having at least three functional groups. The polyisocyanate, for example, can be selected from aromatic toluene diisocyanate and its derivatives used in wall formation for encapsulates, or aliphatic monomer, oligomer or prepolymer, for example, hexamethylene diisocyanate and dimers or trimers thereof, or 3,3,5-trimethyl-5-isocyanatomethyl-1-isocyanato cyclohexane tetramethylene diisocyanate. The polyisocyanate can be selected from 1,3-diisocyanato-2-methylbenzene, hydrogenated MDI, bis(4-isocyanatocyclohexyl)methane, dicyclohexylmethane-4,4'-diisocyanate, and oligomers and prepolymers thereof. This listing is illustrative and not intended to be limiting of the polyisocyanates useful in the invention. Mixtures of the foregoing can also be advantageously used.

Polyisocyanates, for purposes of the invention, are understood as encompassing any polyisocyanate having at least two isocyanate groups and comprising an aliphatic or aromatic moiety in the monomer, oligomer or prepolymer. If aromatic, the aromatic moiety can comprise a phenyl, a toluyl, a xylyl, a naphthyl or a diphenyl moiety, more preferably a toluyl or a xylyl moiety. Aromatic polyisocyanates, for purposes hereof, can include diisocyanate derivatives such as biurets and polyisocyanurates. The polyisocyanate, when aromatic, can be, but is not limited to, methylene diphenyl isocyanate, toluene diisocyanate, tetramethylxylidene diisocyanate, polyisocyanurate of toluene diisocyanate (commercially available from Bayer under the tradename Desmodur® RC), trimethylol propane-adduct of toluene diisocyanate (commercially available from Bayer under the tradename Desmodur® L75), trimethylol propane-adduct of xylylene diisocyanate (commercially available from Mitsui Chemicals under the tradename Takenate® D-110N), naphthalene-1,5-diisocyanate, and phenylene diisocyanate.

Aliphatic polyisocyanate is understood as a polyisocyanate which does not comprise any aromatic moiety. There is a preference for aromatic polyisocyanate. However, aliphatic polyisocyanates and blends thereof are useful. Aliphatic polyisocyanates include a trimer of hexamethylene diisocyanate, a trimer of isophorone diisocyanate, a trimethylol propane-adduct of hexamethylene diisocyanate (available from Mitsui Chemicals), or a biuret of hexamethylene diisocyanate (commercially available from Bayer under the tradename Desmodur® N 100).

The core material of the microcapsules described herein can be a liquid benefit agent dissolvable or dispersible in the oil phase, or a hydrophobic liquid or lipophilic/hydrophobic liquid or even a solid material. The core material typically is an active material and the intended benefit agent.

The core material of the liquid or solid benefit agent is surrounded with a polymeric shell or alternatively embedded in a matrix of the polymer shell or even in a secondary polymer or gel.

Release is achieved through fracture, diffusion or other chemical or physical factors. In some embodiments, retention over a prolonged time period is desirable.

The core material of benefit agent or active material can be the sole, the majority or the minority constituent encapsulated by the microcapsules. In some cases, the benefit agent is diluted with a diluent oil from 0.01 to 99.9 weight percent of the core material. In some cases, the benefit agent can be effective even at trace quantities. A partitioning modifier, optionally, can be included to aid encapsulation and retention of the core material.

The capsules according to the invention are useful with a wide variety of capsule contents ("core materials" or "benefit agents") including, by way of illustration and without limitation, internal phase oils, solvent oils, phase change materials, lubricants, dyes, perfumes, fragrances, cleaning oils, polishing oils, flavorants, nutrients, sweeteners, chromogens, pharmaceuticals, fertilizers, herbicides, biological actives, scents, and the like. The microcapsule core materials can include materials which alter rheology or flow characteristics or extend shelf life or product stability. Essential oils as core materials can include, for example, by way of illustration and without limitation, wintergreen oil, cinnamon oil, clove oil, lemon oil, lime oil, orange oil, peppermint oil and the like. Dyes can include fluorans, lactones, indolyl red, I6B, leuco dyes, all by way of illustration and not limitation. The core material typically should be dispersible or sufficiently soluble in the capsule internal phase material namely in the internal phase oil or soluble or dispersible in the monomers or oligomers solubilized or dispersed in the internal phase oil. The core materials are preferably liquid but can be solid depending on the materials selected, and with temperatures appropriately adjusted to effect dispersion.

Useful benefit agents or core materials include perfume, raw materials, such as alcohols, ketones, aldehydes, esters, ethers, nitriles, alkenes, fragrances, fragrance solubilizers, essential oils, phase change materials, lubricants, colorants, cooling agents, preservatives, antimicrobial or antifungal actives, herbicides, antiviral actives, antiseptic actives, biological actives, deodorants, emollients, humectants, exfoliants, ultraviolet absorbing agents, self-healing compositions, corrosion inhibitors, silicone oils, waxes, hydrocarbons, higher fatty acids, essential oils, lipids, skin coolants, vitamins, sunscreens, antioxidants, glycerine, catalysts, bleach particles, silicon dioxide particles, malodor reducing agents, dyes, brighteners, antibacterial actives, antiperspirant actives, cationic polymers and mixtures thereof. Phase change materials useful as core materials can include, by way of illustration and not limitation, paraffinic hydrocarbons having 13 to 28 carbon atoms, various hydrocarbons such n-octacosane, n-heptacosane, n-hexacosane, n-pentacosane, n-tetracosane, n-tricosane, n-docosane, n-heneicosane, n-eicosane, n-nonadecane, octadecane, n-heptadecane, n-hexadecane, n-pentadecane, n-tetradecane, n-tridecane. Phase change materials can alternatively, optionally in addition include crystalline materials such as 2,2-dimethyl-1,3-propanediol, 2-hydroxymethyl-2-methyl-1, 3-propanediol, acids of straight or branched chain hydrocarbons such as eicosanoic acid and esters such as methyl palmitate, fatty alcohols and mixtures thereof. Blends of capsule populations can be useful, such as with differing sets of benefit agent, or even different wall formulations.

A partitioning modifier can optionally be included as a constituent of the microcapsule core. The partitioning modifier can be the same material as the oil phase or diluent, or can be different. The microcapsules may encapsulate a partitioning modifier in addition to the benefit agent. Non-limiting examples of partitioning modifiers include isopropyl myristate, mono-, di-, and tri-esters of C4-C24 fatty acids, castor oil, mineral oil, soybean oil, hexadecanoic acid, methyl ester isododecane, isoparaffin oil, polydimethylsiloxane, brominated vegetable oil, and combinations thereof. Microcapsules may also have varying ratios of the partitioning modifier to the benefit agent so as to make different populations of microcapsules that may have different bloom patterns. Such populations may also incorporate different perfume oils so as to make populations of microcapsules that display different bloom patterns and different scent experiences. US 2011/0268802 A1 discloses other non-limiting examples of microcapsules and partitioning modifiers and is hereby incorporated by reference.

Optionally, the partitioning modifier can be selected from the group consisting of oil soluble materials that have a C log P greater than 4, 5, 7, or even 11 and/or materials that also have a density higher than 1 g/cm$^3$.

An emulsion containing the first aqueous solution, the second aqueous solution and the oil phase can be prepared by different processes.

One process to produce the emulsion is first combining the first aqueous solution containing the emulsifier and the second aqueous solution containing the PBAE prepolymer under mixing, and then adding the oil phase containing the active material and the polyisocyanate into the aqueous mixture of the first aqueous solution and the second aqueous solution. The resultant mixture is milled under high shear agitation at a speed from about 2000 to 4000 rpm at a temperature of 5-55° C. The milling under high shear agitation may take 6 to 61 mins or even longer until a target particle size is reached and the emulsion is stable. Milling is then stopped and mixing continued. Mixing may continue up to several hours.

Alternatively, another process to produce the emulsion is first mixing the first aqueous solution containing the emulsifier and the oil phase containing the active material and the polyisocyanate. Milling the resultant mixture under high shear agitation at a speed typically from 2000 to 4000 rpm at a temperature of 5-55° C. The milling may take 6 to 61 mins or even longer until a target particle size is reached and the emulsion is stable. Milling under high shear agitation is then stopped. Next, the second aqueous solution containing the PBAE prepolymer is mixed into the emulsion containing the first aqueous solution and the oil phase.

In some embodiments, the milling speed under high shear agitation is 2000 rpm, 2500 rpm, 3000 rpm, or 4000 rpm. In some embodiments, the milling temperature is 5° C., 15° C., 25° C., or 35° C. In some embodiments, the milling takes 6 mins, 7 mins, 10 mins, 12 mins, 61 mins or longer.

Meanwhile, a third aqueous solution is prepared by dissolving a multifunctional acrylate or a mixture of mono-functional and multifunctional acrylates or a mixture of multifunctional acrylate, such as a bifunctional acrylate, or/and a trifunctional acrylate, or/and a monofunctional acrylate in water.

As used herein, reference to the term "acrylate" or "acrylic" is to be understood as referring to acrylate of the specified monomer, oligomer and/or prepolymer. For example multifunctional acrylate, alkyl esters of acrylic acid, and polyacrylate. Each alkyl moiety herein, unless otherwise indicated, can be from $C_1$ to $C_8$, or even from $C_1$ to $C_{24}$. Polyacrylate materials are intended to encompass a broad spectrum of polymeric materials including, for example, polyester polyacrylates, urethane and polyurethane polyacrylates (especially those prepared by the reaction of an hydroxyalkyl acrylate with a polyisocyanate or a urethane polyisocyanate), methyl cyanoacrylate, ethyl cyanoacrylate, diethylene glycol diacrylate, trimethylolpropane triacrylate, ethylene glycol diacrylate, allyl acrylate, glycidyl acrylate, acrylate functional silicones, di-, tri- and tetra ethylene glycol diacrylate, dipropylene glycol diacrylate, polyethylene glycol diacrylate, di(penta methylene glycol) diacrylate, ethylene diacrylate, neopentyl glycol diacrylate, trimethylolpropane triacrylate, ethoxylated bisphenol A diacrylates, bisphenol A diacrylates, digylcerol diacrylate, tetra ethylene glycol dichloroacrylate, 1,3-butanediol diacrylate, neopentyl diacrylate, trimethylolpropane triacrylate, polyethylene glycol diacrylate, dipropylene glycol diacrylate, various multifunctional acrylates, and multifunctional amine acrylates.

Non-limiting examples of multifunctional acrylate monomers, oligomers and prepolymers thereof include ethylene glycol diacrylate, triylolpropane triacrylate, trimethylolpropane triacrylate, pentaerythritol tetraacrylate, tricyclodecane dimethanol diacrylate, 1,10 decanediol diacrylate, 1,6 hexanediol diacrylate, 1,9 nonanediol diacrylate, neopentyl glycol diacrylate, di-trimethylolpropane tetraacrylate, dipentaerythritol pentaacrylate, ethoxylated (2) bisphenol A diacrylate, 2,2 bis[4-(acyloyl ethoxy) phenyl]propane, ethoxylated (3) bisphenol A diacrylate, dipropylene glycol diacrylate, ethoxylated (4) bisphenol A diacrylate, ethoxylated (4) bisphenol A diacrylate, 2,2 bis[4-(acyloyl ethoxy) phenyl] propane, pentaerythritol triacrylate, polyethylene glycol 200 diacrylate, ethoxylated (9) trimethylolpropane triacrylate, 2,2 bis[4-(acyloyl ethoxy) phenyl] propane, ethoxylated (30) BPA diacrylate, ethoxylated (15) trimethylolpropane triacrylate, ethoxylated glycerine triacrylate, ethoxylated (20) trimethylolpropane triacrylate, polyethylene glycol 400 diacrylate, polyethylene glycol 600 diacrylate, ethoxylated glycerine triacrylate, ethoxylated pentaerythritol tetraacrylate, polyethylene glycol 1000 diacrylate, polyethylene (200) glycol diacrylate, polyethylene glycol (200) diacrylate, polyethylene glycol (400) diacrylate, polyethylene glycol (600) diacrylate and tris (2-hydroxy ethyl) isocyanurate triacrylate, diethylene glycol diacrylate, ethoxylated (3) trimethylolpropane triacrylate, polypropylene glycol 400 diacrylate, ethoxylated (10) bisphenol A diacrylate, ethoxylated (10) bisphenol A diacrylate, 2,2 bis[4-(acryloyl ethoxy) phenyl] propane, ethoxylated (4) pentaerythritol tetraacrylate, triethylene glycol diacrylate, 2-hydroxyl 1-3 diacryloxy propane, ethoxylated (6) trimethylolpropane triacrylate, ethoxylated propyleneglycol diacrylate, 2,2 bis[4-(acryloyl ethoxy) phenyl] propane and the like, and mixtures of any of the foregoing.

In some embodiments, the bifunctional acrylate is Diethylene glycol diacrylate (SR230, Sartomer), Trifunctional trimethylolpropane triacrylate (SR351, Sartomer), Ethoxylated trimethylolpropane triacrylate (SR415, Sartomer), Ethoxylated trimethylolpropane triacrylate (SR454, Sartomer), pentaerythritol triacrylate (SR444, Sartomer), or pentaerythritol tetraacrylate (SR295, Sartomer).

Once the emulsion containing the first aqueous solution, the second aqueous solution and the oil phase is obtained, mix the third aqueous solution with the emulsion at a temperature of 25-50° C. In one embodiment, this temperature is 35° C.

Finally, the temperature of the resulted mixture is increased to an elevated temperature of 50-95° C. in a period of time between 30-120 mins, and hold at the elevated temperature for a period of time of 2-24 hours. Exemplary elevated temperatures can be 50° C., 55° C., 70° C., 75° C., 80° C., 90° C. or 95. In one embodiment, the temperature of the resulted mixture is increased from 35° C. to 75° C. in 60 mins and hold at 75° C. for 8 hours.

In the above described method, polymerization reaction between the amine group of the multifunctional amine and the acrylate group of the multifunctional acrylate in the second aqueous solution occurs to form PBAE prepolymer. Polymerization reaction between polyisocyanate in the oil phase and multifunctional amine in the second aqueous solution occurs to form PU microcapsule shell. Meanwhile, competing reactions, including the reaction between polyisocyanate and the amine moiety of the PBAE, the reaction between the isocyanate group of PU and the amine moiety of the PBAE, the reaction between the amine moiety in the PU backbone and the multifunctional acrylate or the acrylate group of PBAE, occur to form hybrid PU/PBAE. Hybrid PU/PBAE is a copolymer of PU and PBAE, and can include blended polymers or copolymers derived from combinations of the above described various reaction pathways. PBAE can be formed in situ, sequentially or pre-formed separately in advance. The hybrid PU/PBAE have both urea linkage and beta-amino esters linkage. These polymerization reactions may form an inner microcapsule shell of PU and hybrid PU/PBAE.

After a third aqueous solution containing the multifunctional acrylate is added into the emulsion containing the first aqueous solution, the second aqueous solution and the oil phase, the excess multifunctional acrylate in the third aqueous solution may further react with any primary or secondary amine moiety of PBAE prepolymer. In addition, the multifunctional acrylate may further crosslink PBAE in the aqueous solution with the PU and hybrid PU/PBAE in the inner microcapsule shell. These reactions may lead to the formation of an outer microcapsule shell of PBAE, which crosslinks to the inner microcapsule shell of PU and hybrid PU/PBAE.

As produced in this invention, the PU/PBAE microcapsule may have a single or dual shell structure including an inner shell or surface and an outer shell or surface. The PBAE in the outer shell or surface is crosslinked with the PU and hybrid PU/PBAE in the inner shell or surface by the multifunctional acrylate in the third aqueous solution. Other crosslinking reactions include the reaction between acrylate moiety of PBAE with the amine moiety on the backbone of PU or the amine moiety of hybrid PU/PBAE, and the amine moiety of PBAE with isocyanate group of PU or the acrylate moiety of hybrid PU/PBAE. All these crosslinking reactions may contribute incorporating PBAE in the outer shell or surface into PU and hybrid PU/PBAE in an inner shell or surface.

In a method of making the PU/PBAE microcapsules, the multifunctional acrylate may be not included in the second aqueous solution. If the multifunctional acrylate is not included in the second aqueous solution, PBAE prepolymer is not formed in the second aqueous solution. The polymerization reaction between polyisocyanate in the oil phase and the multifunctional amine in the second aqueous solution occurs to form an inner microcapsule shell of PU.

After the third aqueous solution containing a multifunctional acrylate is added into the emulsion, polymerization reaction between the multifunctional amine and the multifunctional acrylate occurs to form PBAE in the aqueous phase. As a result, hybrid PU/PBAE is formed in the reactions between the multifunctional acrylate and the amine moiety in the PU backbone, the acrylate group of PBAE and the amine moiety in the PU backbone, the isocyanate group of PU and the amine moiety of the PBAE. These reactions may lead to the formation of a transitional microcapsule shell of hybrid PU/PBAE.

In addition, further crosslinking reaction between the amine moiety of PBAE in the aqueous phase and the amine moiety of the hybrid PU/PBAE in the transitional microcapsule shell by the multifunctional acrylate may lead to the formation of an outer microcapsule shell of PBAE.

As such, the method of making the PU/PBAE microcapsules in the present invention may generate a PU/PBAE microcapsule with an inner shell of PU, a transitional shell of hybrid PU/PBAE and an outer shell of PBAE.

In a method of making the PU/PBAE microcapsules in this invention, the third aqueous solution containing a multifunctional acrylate may not be provided and not be added into the emulsion containing the first aqueous solution, the second aqueous solution and the oil phase. In this method, the second aqueous contains a multifunctional acrylate. The PU/PBAE microcapsule formed in the method absent of the third aqueous solution may have a single microcapsule shell of PU and hybrid PU/PBAE.

The final product of the PU/PBAE microcapsules is a slurry having oily medium-containing microcapsules encapsulated by PU/PBAE polymer dispersed in the aqueous medium.

FIG. 1 shows a cross-section of the shell structure of a fractured microcapsule in the middle and upper region of the SEM image. The shell of the microcapsule has two visible layers/shells for this particular embodiment.

The microcapsule size distribution was measured using a light diffraction instrument. As measured, the PU/PBAE microcapsules of the present invention have a particle size between 2-200 µm with a median particle size of 3-100 µm.

Figure 2:
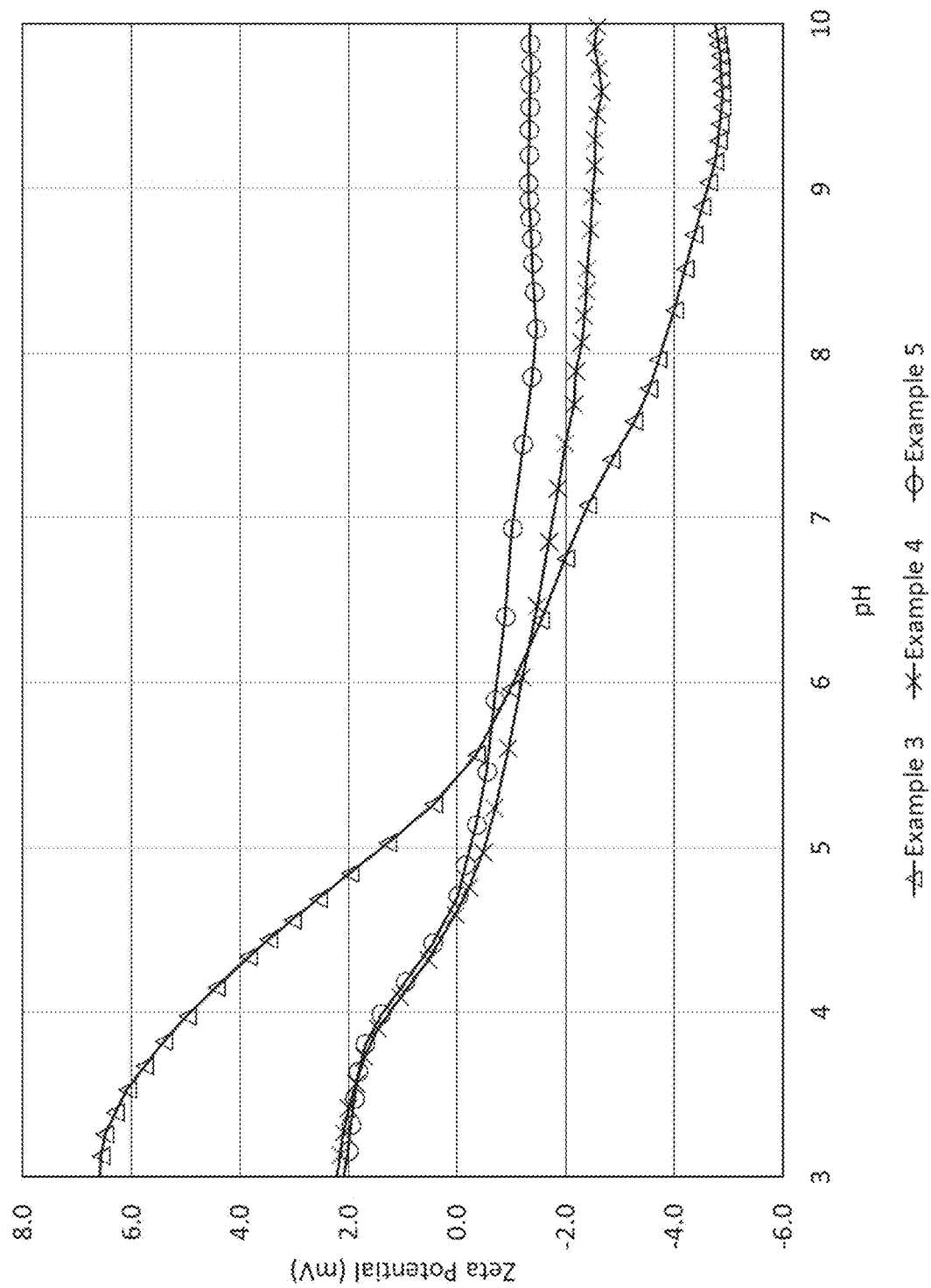
FIG. 2 shows the zeta potentials of the PU/PBAE microcapsules produced in Examples 3, 4 and 5 of the present invention.

In order to test the properties of the PU/PBAE microcapsules of the present invention, the PU/PBAE microcapsules were subjected to a plurality of tests. FIG. 2 shows that the zeta potential of the PU/PBAE microcapsule is −100 mV-+200 mV at pH 3 and −200 mV-+100 mV at pH 10.

Tables 2-4 show the slurry results including the solids in the slurry, free core, 1 week leakage, and 90 mins release for the PU/PBAE microcapsules produced in the Examples of the present invention as described below. U.S. Pat. No. 10,415,000 B2 and U.S. Pat. No. 10,485,739 B2 disclose the methods of the measurements for the microcapsules and are hereby incorporated by reference.

Surface charge optionally can be built into the microcapsule shells with selection of monomers, or optionally added to the microcapsules with deposition aids or charged groups to improve the deposition of the microcapsules on substrates such as textiles, skin, hair, fibers, or other surfaces. The microcapsules can be over coated with the deposition aids as a post-encapsulation step such as by blending or mixing following or during the latter capsule formation steps. In certain embodiments the resultant microcapsules are cationic. Surface charge can also be advantageously employed to improve adhesion of microcapsules on surfaces such as foam or bedding material.

Deposition aids can include poly (acrylamide-co-diallyldimethylammonium chloride, poly (diallyldimethylammonium chloride, polyethylenimine, cationic polyamine, poly [(3-methyl-1-vinylimidazolium chloride)-co-(1-vinylpyrrolidone)], copolymer of acrylic acid and diallyldimethylammonium chloride, cationic guar, guar gum, an organopolysiloxane such as described in US Patent Application Publication 2015/0030557, incorporated herein by reference. In a further embodiment, the above-described microcapsules can comprise a deposition aid, and in a further aspect the deposition aid coats the outer surface of the shell of the microcapsule. Deposition aids can be coated onto capsules or covalently bonded, employing functional groups to effect linkage as generally described in Universidade do Minho, WO 2006117702; Gross et al., US 20170296440; and Universidade do Minho, US 20080193761.

In a further aspect, the deposition aid can comprise a material selected from the group consisting of poly(meth) acrylate, poly(ethylene-maleic anhydride), polyamine, wax, polyvinylpyrrolidone, polyvinylpyrrolidone co-polymers, polyvinylpyrrolidone-ethyl acrylate, polyvinylpyrrolidone-vinyl acrylate, polyvinylpyrrolidone methacrylate, polyvinylpyrrolidone-vinyl acetate, polyvinyl acetal, polyvinyl butyral, polysiloxane, poly(propylene maleic anhydride), maleic anhydride derivatives, co-polymers of maleic anhydride derivatives, polyvinyl alcohol, styrene-butadiene latex, gelatin, gum Arabic, carboxymethyl cellulose, carboxymethyl hydroxyethyl cellulose, hydroxyethyl cellulose, other modified celluloses, sodium alginate, chitosan, casein, pectin, modified starch, polyvinyl acetal, polyvinyl butyral, polyvinyl methyl ether/maleic anhydride, polyvinyl pyrrolidone and its co polymers, poly(vinyl pyrrolidone/methacrylamidopropyl trimethyl ammonium chloride), polyvinylpyrrolidone/vinyl acetate, polyvinyl pyrrolidone/ dimethylaminoethyl methacrylate, polyvinyl amines, polyvinyl formamides, polyallyl amines and copolymers of polyvinyl amines, polyvinyl formamides, and polyallyl amines and mixtures thereof.

In a yet further aspect, the deposition aid comprises a material selected from the group consisting of poly(meth) acrylates, poly(ethylene-maleic anhydride), polyamine, polyvinylpyrrolidone, polyvinylpyrrolidone-ethyl acrylate, polyvinylpyrrolidone-vinyl acrylate, polyvinylpyrrolidone methacrylate, polyvinylpyrrolidone-vinyl acetate, polyvinyl acetal, polysiloxane, poly(propylene maleic anhydride), maleic anhydride derivatives, co-polymers of maleic anhydride derivatives, polyvinyl alcohol, carboxymethyl cellulose, carboxymethyl hydroxyethyl cellulose, hydroxyethyl cellulose, polyvinyl methyl ether/maleic anhydride, polyvinylpyrrolidone/vinyl acetate, polyvinyl pyrrolidone/dimethylaminoethyl methacrylate, polyvinyl amines, polyvinyl formamides, polyallyl amines and copolymers of polyvinyl amines, polyvinyl formamides, and polyallyl amines and mixtures thereof.

Surface charge can also be advantageously adapted to create agglomerates to facilitate ease of filtration where a high solids, cake, or dry powder of microcapsules is desirable.

If desired, the microcapsules can be separated from the aqueous medium. The microcapsules can either be used as in an aqueous slurry, used as a dewatered cake, or used in dry powder form depending on the application.

The microcapsules of the invention can be incorporated dry, as an aqueous slurry, as a coating or as a gel into a variety of commercial products to yield novel and improved articles of manufacture, including incorporation into or onto foams, mattresses, bedding, cushions, added to cosmetics or to medical devices, incorporation into or onto packaging, dry wall, construction materials, heat sinks for electronics, cooling fluids, incorporation into insulation, used with lotions, incorporation into gels including gels for coating fabrics, automotive interiors, and other structures or articles, including clothing, footwear, personal protective equipment and any other article where use of the improved capsules of the invention is deemed desirable. The articles of manufacture can be selected from the group consisting of a soap, a surface cleaner, a laundry detergent, a fabric softener, a shampoo, a textile, a paper towel, an adhesive, a wipe, a diaper, a feminine hygiene product, a facial tissue, a pharmaceutical, a napkin, a deodorant, a foam, a pillow, a mattress, bedding, a cushion, a cosmetic, a medical device, an agricultural product, packaging, a cooling fluid, a wallboard, and an insulation.

The microcapsules protect and separate the core material, such as phase change material or fragrance or other core material or benefit agent, from the external environment. This facilitates design of distinct and improved articles of manufacture. The microcapsules facilitate improving flowability of encapsulated materials and enhancing ease of incorporation into or onto articles such as foams, gels, textiles, various cleaners, detergents or fabric softeners. The microcapsules can be used neat, or more often blended into coatings, gels or used as an aqueous slurry or blended into other articles to form new and improved articles of manufacture. For example, with phase change benefit agents, the microcapsules help preserve the repeated activity of the phase change material and retain the phase change material to prevent leakage or infusion into nearby components when isolation of the microcapsules is desired, yet promote eventual degradation of such encapsulates or portions of the articles of manufacture.

The shell of the composition according to the invention can achieve at least 10% degradation or greater after as little as 28 days when tested according to test method OECD TG 301B. A surprising aspect is that capsules formed are not only tight capsules with low leakage but such capsules exhibit degradable properties in relatively short time periods. Microcapsules according to the invention are of enhanced degradability as compared to capsules according to the prior art.

Procedure for Determination of Free Core Oil

The following method measures the amount of oil in the water phase. 1 mg/ml dibutyl phthalate (DBP)/hexane is used as an internal standard solution.

Weigh a little more than 250 mg DBP into a small beaker and then transfer the DBP into a 250 ml beaker. Fill the beaker with hexane to 250 ml.

Sample Prep: Weigh approximately 1.5-2 gram microcapsule slurry (40 drops) into a 20 ml scintillation vial, add 10 ml internal standard solution, and cap tightly. Shaking the vial vigorously several times over 30 minutes. Pipette the solution into an autosampler vial and analyze by gas chromatography (GC).

Instrumentation: HP5890 GC connected to HP Chem Station Software; Column: 5 m×0.32 mm id with 1 μm DB-1 liquid phase; Keep the temperature of the sample at 50° C. for 1 minute then increase the temperature to 320° C. at the speed of 15° C./min; Injector temperature is 275° C.; Detector temperature is 325° C.; Measurements have been performed with 2 ul injection.

Calculation: Add total peak area minus the area for the DBP for both the sample and calibration. The following equation is used to calculate mg of free core oil:

$$\frac{\text{Total area from sample}}{\text{Total area from calibration}} \times \text{mg of oil in calibration solution} = \text{mg of free oil}$$

The following equation is used to calculate % free core oil:

$$\frac{\text{mg of free core oil}}{\text{Sample wt. (mg)}} \times 100 = \% \text{ free core oil in wet slurry}$$

The obtained values are shown in Table 2 as % free core.

Procedure for Determination of Benefit Agent Leakage

Obtain two microcapsule compositions encapsulating benefit agent, each weighs one gram. Add one microcapsule composition of 1 gram (Sample 1) to 99 grams of product matrix in which the microcapsule will be employed. Age the microcapsule containing product matrix (Sample 1) for applicable measurement time period at 35° C. in a sealed glass jar. The other 1 gram microcapsule composition (Sample 2) is similarly aged.

After one week (or 90 minutes for 90 min leakage), use filtration to recover the microcapsule composition's microcapsules from the product matrix (Sample 1) and from the microcapsule composition (Sample 2). Treat each microcapsule composition with a solvent that will extract all the benefit agent from each sample. Inject the benefit agent containing solvent from each sample into a Gas Chromatograph and integrate the peak areas to determine the total quantity of benefit agent extracted from each sample.

Determine the percentage of benefit agent leakage by calculating the difference of the quantity of benefit agent extracted from Sample 2 and Sample 1, expressed as a percentage of the total quantity of benefit agent extracted from Sample 2, as represented in the equation below:

$$\text{Percentage of Benefit Agent Leakage} = \left(\frac{\text{Sample 2} - \text{Sample 1}}{\text{Sample 2}}\right) \times 100$$

The values reported in Table 2 are % leakage (by weight) of the active material, used synonymously as benefit agent.

Procedure for Determination of Degradation

Degradation is determined by the "Organization for Economic Co-operation and Development (OECD) Guideline for Testing of Chemicals" 301B CO2 Evolution (Modified Sturm Test), adopted 17 Jul. 1992. For ease of reference, this test method is referred to herein as test method OECD 301B.

In Tables 3, 4, and 5 herein, data is presented as 28 day degradation/%. Data of % degradation can also be similarly constructed at differing time frames such as 60 day degradation/%.

EXAMPLES

Examples of the PU/PBAE microcapsules are produced as set forth below. Table 1 sets forth the ingredient list of key ingredients employed in the Examples. Table 2, Table 3, Table 4 and Table 5 present the formulations for each of water phase I (WPI), water phase II (WPII), oil phase and water phase III (WPIII) employed in Examples 1-7, 8-14, 15-19 and 20-27 respectively. The units of the ingredients in Table 2, 3, 4, and 5 are grams, and measurements are by weight, unless noted otherwise.

TABLE 1

| Tradename | Description | Manufacture |
| --- | --- | --- |
| SR230 | Diethylene glycol diacrylate | Sartomer |
| SR351 | Trifunctional trimethylolpropane triacrylate | Sartomer |
| SR415 | Ethoxylated trimethylolpropane triacrylate | Sartomer |
| SR454 | Ethoxylated trimethylolpropane triacrylate | Sartomer |
| Captex 355 | Medium-chain triglyceride based on caprylic and capric acids | Abitec Corporation |
| Aromatic 200 | Aromatic hydrocarbon | Exxon mobil |
| Desmodur W | Dicyclohexylmethane diisocyanate | Covestro AG |
| Takenate D110N | Aliphatic polyisocyanate adduct prepolymer based on xylyene diisocyanate | Mitsui Chemicals |
| Desmodur N3400 | Aliphatic polyisocyanate (Hexamethylene diisocyanate uretdione) | Covestro AG |

Example 2

Hybrid PU/PBAE microcapsules that encapsulate a fragrance and Captex 355 are produced in the following steps:
WPI is prepared in the same way as in Example 1.
WPII is prepared in a reactor by mixing DETA in water for 5 mins, and then SR230 is slowly added into the DETA solution under mixing at 35 C°. Start timer after all SR230 is added and mix WPII at 35 C.° for 140 mins.
Add WPI into WPII and mix for 10 mins. The total reaction between SR230 and DETA to form PBAE prepolymer is 150 mins at 35° C.
Oil Phase is prepared in the same way as in Example 1.
Oil Phase is added to the mixture of WPI and WPII at 1200 rpm. Start applying high shear agitation at 4000 rpm at 35 C.° after all of the Oil Phase is added to form an emulsion. Stop high shear agitation and switch to mixing once desired particle size is reached.
Add WPIII containing SR230 dropwisely into the emulsion under mixing at 35 C°.
Increasing temperature after all WPIII is added from 35 C.° to 75 C.° in 60 mins and hold at 75 C.° for 8 hours while mixing at 680 rpm.

Example 3

Hybrid PU/PBAE microcapsules that encapsulate a fragrance and Captex 355 are produced in the following steps:
WPII is prepared in the same way as in Example 1.
WPI is prepared in the same way as in Example 1 in a reactor under mixing.
Oil Phase is prepared by mixing the fragrance and Captex 355 and Takenate D110N at room temperature.
Oil Phase is added to WPI in the reactor at 1000 rpm. Start applying high shear agitation at 2500 rpm at 25° C. after all the Oil Phase is added to form an emulsion. Stop high shear agitation and switch to mixing once desired particle size is reached.
WPII is then added to the emulsion in the reactor and warmed up to 35° C. under mixing.
Add WPIII containing SR230 dropwisely into the reactor under mixing at 35° C. after the addition of WPII.
Increasing temperature after all WPIII is added from 35° C. to 75° C. in 60 mins and hold at 75° C. for 8 hours while mixing at 600 rpm.

Example 4

Hybrid PU/PBAE microcapsules that encapsulate a perfume and Isopropyl myristate are produced in the following steps:
WPII is prepared in the same way as in Example 1.
WPI is prepared in the same way as in Example 1 in a reactor under mixing.
Oil Phase is prepared by mixing the perfume, Isopropyl myristate and Takenate D110N at room temperature.
Oil Phase is added to WPI in the reactor at 1000 rpm. Start applying high shear agitation at 2500 rpm at 25° C. after all the Oil Phase is added to form an emulsion. Stop high shear agitation at t=6 mins and switch to mixing.
WPII is then added to the emulsion in the reactor and warmed up to 35° C. under mixing.
Add WPIII containing SR230 dropwisely into the emulsion under mixing at 35° C.
Increasing temperature after all WPIII is added from 35° C. to 75° C. in 60 mins and hold at 75° C. for 8 hours under mixing.

Example 5

Hybrid PU/PBAE microcapsules that encapsulate a perfume and Isopropyl myristate are produced in the following steps:
WPII is prepared in the same way as in Example 1.
WPI is prepared in the same way as in Example 1 in a reactor under mixing.
Oil Phase is prepared in the same way as in Example 4.
Oil Phase is added to WPI in the reactor at 1000 rpm. Start applying high shear agitation at 2000 rpm at 25° C. after all the Oil Phase is added to form an emulsion. Stop high shear agitation at t=7 mins and switch to mixing at 600 rpm.
WPII is then added to the emulsion in the reactor and warmed up to 35° C. under mixing at 500 rpm.
Add WPIII containing SR351 dropwisely into the reactor under mixing at 35° C.
Increasing temperature after all WPIII is added from 35° C. to 75° C. in 60 mins and hold at 75° C. for 8 hours under mixing.

Example 6

Hybrid PU/PBAE microcapsules that encapsulate Nitrapyrin and Aromatic 200 (ExxonMobil, Irving, TX) are produced in the following steps:
WPI is prepared in the same way as in Example 1.
WPII is prepared in the same way as in Example 1 in a reactor under mixing.
Add WPI into WPII and mix for 10 mins at 35° C. The total reaction between SR230 and DETA to form PBAE prepolymer is 90 mins at 35 C°.
Oil Phase is prepared by mixing Nitrapyrin, Aromatic 200 and Desmodur W at room temperature.

Oil Phase is added into the mixture of WPI and WPII at 1200 rpm at 35° C. Start applying high shear agitation at 4000 rpm at 35 C.° after all of the Oil Phase is added to form an emulsion. Stop high shear agitation at t=10 mins and switch to mixing.

Add WPIII containing SR230 dropwisely into the emulsion under mixing at 35 C°.

Increasing temperature after all WPIII is added from 35° C. to 75° C. in 60 mins and hold at 75° C. for 8 hours under mixing.

Example 7

Hybrid PU/PBAE microcapsules that encapsulate Nitrapyrin and Aromatic 200 are produced in the following steps:

WPI is prepared in the same way as in Example 1 in a reactor under mixing.

WPII is prepared in the same way as in Example 1.

Oil Phase is prepared by mixing Nitrapyrin, Aromatic 200 and Takenate D110N at room temperature.

Oil Phase is added to WPI in the reactor at 1000 rpm. Start applying high shear agitation at 3000 rpm at 25° C. after all the Oil Phase is added to form an emulsion. Stop high shear agitation at t=12 mins and switch to mixing.

WPII is then added into the emulsion in the reactor and then warmed up to 35° C. under mixing at 650 rpm.

Add WPIII containing SR230 dropwisely into the reactor under mixing at 35° C.

Increasing temperature after all WPIII is added from 35° C. to 75° C. in 60 mins and hold at 75° C. for 8 hours under mixing.

Example 8

Hybrid PU/PBAE microcapsules that encapsulate Nitrapyrin and Aromatic 200 are produced in the following steps:

WPI is prepared in the same way as in Example 1 in a reactor under mixing.

WPII is prepared in the same way as in Example 1.

Oil Phase is prepared in the same way as in Example 7.

Oil Phase is added to WPI in the reactor at 1000 rpm. Start applying high shear agitation at 4000 rpm at 15° C. after all the Oil Phase is added to form an emulsion. Stop high shear agitation at t=61 mins and switch to mixing.

WPII is then added to the emulsion in the reactor and then warmed up to 35° C. under mixing at 625 rpm.

Add WPIII containing SR230 dropwisely into the reactor under mixing at 35° C.

Increasing temperature after all WPIII is added from 35° C. to 75° C. in 60 mins and hold at 75° C. for 8 hours under mixing.

Example 9

Hybrid PU/PBAE microcapsules that encapsulate a fragrance and Captex 355 are produced in the following steps:

WPI is prepared in the same way as in Example 1.

WPII is prepared in a reactor by mixing DETA in water for 5 mins, and then SR230 is slowly added into the DETA solution under mixing at 35 C°. Start timer after all SR230 is added and mix WPII at 35 C.° for 90 mins.

Add WPI into WPII and mix for 10 mins in reactor

Oil Phase is prepared in the same way as in Example 1.

Oil Phase is added to the mixture of WPI and WPII at 1200 rpm. Start applying high shear agitation at 4000 rpm at 35 C.° after all of the Oil Phase is added to form an emulsion. Stop high shear agitation and switch to mixing once desired particle size is reached.

Add WPIII containing SR351 dropwisely into the emulsion under mixing at 35 C°.

Increasing temperature after all WPIII is added from 35 C.° to 75 C.° in 60 mins and hold at 75 C.° for 8 hours under mixing.

Example 10

Hybrid PU/PBAE microcapsules that encapsulate a fragrance and Captex 355 are produced in the following steps:

WPI is prepared in the same way as in Example 1.

WPII is prepared in a reactor by mixing DETA in water for 5 mins, and then SR230 is slowly added into the DETA solution under mixing at 35 C°. Start timer after all SR230 is added and mix WPII at 35 C.° for 150 mins.

Add WPI into WPII and mix for 10 mins in reactor

Oil Phase is prepared in the same way as in Example 1.

Oil Phase is added to the mixture of WPI and WPII at 1200 rpm. Start applying high shear agitation at 4000 rpm at 35 C.° after all of the Oil Phase is added to form an emulsion. Stop high shear agitation and switch to mixing once desired particle size is reached.

Add WPIII containing SR351 dropwisely into the emulsion under mixing at 35 C°.

Increasing temperature after all WPIII is added from 35 C.° to 75 C.° in 60 mins and hold at 75 C.° for 8 hours under mixing.

Example 11

Hybrid PU/PBAE microcapsules that encapsulate a fragrance and Captex 355 are produced in the following steps:

WPI is prepared in the same way as in Example 1.

WPII is prepared in a reactor by mixing DETA in water for 5 mins, and then SR230 is slowly added into the DETA solution under mixing at 35 C°. Start timer after all SR230 is added and mix WPII at 50 C.° for 150 mins.

Add WPI into WPII and mix for 10 mins in reactor

Oil Phase is prepared in the same way as in Example 1.

Oil Phase is added to the mixture of WPI and WPII at 1200 rpm. Start applying high shear agitation at 4000 rpm at 35 C.° after all of the Oil Phase is added to form an emulsion. Stop high shear agitation and switch to mixing once desired particle size is reached.

Add WPIII containing SR351 dropwisely into the emulsion under mixing at 35 C°.

Increasing temperature after all WPIII is added from 35 C.° to 75 C.° in 60 mins and hold at 75 C.° for 8 hours under mixing.

Example 12

Hybrid PU/PBAE microcapsules that encapsulate a fragrance and Captex 355 are produced in the following steps:

WPI is prepared in the same way as in Example 1.

WPII is prepared in a reactor by mixing DETA in water for 5 mins, and then SR230 is slowly added into the DETA solution under mixing at 35 C°. Start timer after all SR230 is added and mix WPII at 50 C.° for 90 mins.

Add WPI into WPII and mix for 10 mins in reactor

Oil Phase is prepared in the same way as in Example 1.

Oil Phase is added to the mixture of WPI and WPII at 1200 rpm. Start applying high shear agitation at 4000 rpm at 35 C.° after all of the Oil Phase is added to form an emulsion. Stop high shear agitation and switch to mixing once desired particle size is reached.

Add WPIII containing SR351 dropwisely into the emulsion under mixing at 35 C.°.

Increasing temperature after all WPIII is added from 35 C.° to 75 C.° in 60 mins and hold at 75 C.° for 8 hours under mixing.

Example 13

Hybrid PU/PBAE microcapsules that encapsulate a fragrance and Captex 355 are produced in the following steps:
WPI is prepared in the same way as in Example 1.
WPII is prepared in the same way as in Example 9.
Add WPI into WPII and mix for 10 mins in reactor
Oil Phase is prepared in the same way as in Example 1.
Oil Phase is added to the mixture of WPI and WPII at 1200 rpm. Start applying high shear agitation at 4000 rpm at 35 C.° after all of the Oil Phase is added to form an emulsion. Stop high shear agitation and switch to mixing once desired particle size is reached.

Add WPIII containing SR351 dropwisely into the emulsion under mixing at 35 C.°.

Increasing temperature after all WPIII is added from 35 C.° to 75 C.° in 60 mins and hold at 75 C.° for 8 hours under mixing.

Example 14

Hybrid PU/PBAE microcapsules that encapsulate a fragrance and Captex 355 are produced in the following steps:
WPI is prepared in the same way as in Example 1.
WPII is prepared in the same way as in Example 9.
Add WPI into WPII and mix for 10 mins in reactor.
Oil Phase is prepared in the same way as in Example 1.
Oil Phase is added to the mixture of WPI and WPII at 1200 rpm. Start applying high shear agitation at 4000 rpm at 35 C.° after all of the Oil Phase is added to form an emulsion. Stop high shear agitation and switch to mixing once desired particle size is reached.

Add WPIII containing SR351 dropwisely into the emulsion under mixing at 35 C.°.

Increasing temperature after all WPIII is added from 35 C.° to 75 C.° in 60 mins and hold at 75 C.° for 8 hours under mixing.

Example 15

Hybrid PU/PBAE microcapsules that encapsulate a fragrance and Captex 355 are produced in the following steps:
WPI is prepared in the same way as in Example 1.
WPII is prepared in the same way as in Example 10.
Add WPI into WPII and mix for 10 mins in reactor
Oil Phase is prepared in the same way as in Example 1.
Oil Phase is added to the mixture of WPI and WPII at 1200 rpm. Start applying high shear agitation at 4000 rpm at 35 C.° after all of the Oil Phase is added to form an emulsion. Stop high shear agitation and switch to mixing once desired particle size is reached.

Increasing temperature from 35 C.° to 75 C.° in 60 mins and hold at 75 C.° for 8 hours under mixing. No WPIII is used in this example.

Example 16

Hybrid PU/PBAE microcapsules that encapsulate a fragrance and Captex 355 are produced in the following steps:
WPI is prepared in the same way as in Example 1.
WPII is prepared in the same way as in Example 10.
Add WPI into WPII and mix for 10 mins in reactor.
Oil Phase is prepared in the same way as in Example 1.
Oil Phase is added to the mixture of WPI and WPII at 1200 rpm. Start applying high shear agitation at 4000 rpm at 35 C.° after all of the Oil Phase is added to form an emulsion. Stop high shear agitation and switch to mixing once desired particle size is reached.

Increasing temperature from 35 C.° to 75 C.° in 60 mins and hold at 75 C.° for 8 hours under mixing. No WPIII is used in this example.

Example 17

Hybrid PU/PBAE microcapsules that encapsulate a fragrance and Captex 355 are produced in the following steps:
WPI is prepared in the same way as in Example 1.
WPII is prepared in the same way as in Example 11.
Add WPI into WPII and mix for 10 mins in reactor.
Oil Phase is prepared in the same way as in Example 1.
Oil Phase is added to the mixture of WPI and WPII at 1200 rpm. Start applying high shear agitation at 4000 rpm at 35 C.° after all of the Oil Phase is added to form an emulsion. Stop high shear agitation and switch to mixing once desired particle size is reached.

Increasing temperature from 35 C.° to 75 C.° in 60 mins and hold at 75 C.° for 8 hours under mixing. No WPIII is used in this example.

Example 18

Hybrid PU/PBAE microcapsules that encapsulate a fragrance and Captex 355 are produced in the following steps:
WPI is prepared in the same way as in Example 1.
WPII is prepared in the same way as in Example 12.
Add WPI into WPII and mix for 10 mins in reactor
Oil Phase is prepared in the same way as in Example 1.
Oil Phase is added to the mixture of WPI and WPII at 1200 rpm. Start applying high shear agitation at 4000 rpm at 35 C.° after all of the Oil Phase is added to form an emulsion. Stop high shear agitation and switch to mixing once desired particle size is reached.

Increasing temperature from 35 C.° to 75 C.° in 60 mins and hold at 75 C.° for 8 hours under mixing. No WPIII is used in this example.

Example 19

Hybrid PU/PBAE microcapsules that encapsulate a fragrance and Captex 355 are produced in the following steps:
WPI is prepared in the same way as in Example 1.
WPII is prepared in the same way as in Example 9.
Add WPI into WPII and mix for 10 mins in reactor
Oil Phase is prepared in the same way as in Example 1.
Oil Phase is added to the mixture of WPI and WPII at 1200 rpm. Start applying high shear agitation at 4000 rpm at 35 C.° after all of the Oil Phase is added to form an emulsion. Stop high shear agitation and switch to mixing once desired particle size is reached.

Increasing temperature from 35 C.° to 75 C.° in 60 mins and hold at 75 C.° for 8 hours under mixing. No WPIII is used in this example.

Example 20

Hybrid PU/PBAE microcapsules that encapsulate a fragrance and Captex 355 are produced in the following steps:

WPI is prepared in the same way as in Example 1.
WPII is prepared in the same way as in Example 1.
Add WPI into WPII and mix for 10 mins in the reactor.
Oil Phase is prepared in the same way as in Example 1 but using Desmodur N3400 as the source of isocyanate.
Oil Phase is added to the mixture of WPI and WPII at 1200 rpm. Start applying high shear agitation at 4000 rpm at 35 C.° after all of the Oil Phase is added to form an emulsion. Stop high shear agitation and switch to mixing once desired particle size is reached.
Add WPIII containing SR230 dropwisely into the emulsion under mixing at 35 C°.
Increasing temperature from 35 C.° to 75 C.° in 60 mins and hold at 75 C.° for 8 hours under mixing.

Example 21

Hybrid PU/PBAE microcapsules that encapsulate a fragrance and Captex 355 are produced in the following steps:
WPI is prepared in the same way as in Example 1.
WPII is prepared in a reactor by mixing Ethylenediamine in water for 5 mins, and then slowly add SR230 into the Ethylenediamine solution under mixing at 35 C°. Start timer after all SR230 is added and mix WPII at 35 C.° for 80 mins.
Add WPI into WPII and mix for 10 mins in reactor
Oil Phase is prepared in the same way as in Example 1.
Oil Phase is added to the mixture of WPI and WPII at 1200 rpm. Start applying high shear agitation at 4000 rpm at 35 C.° after all of the Oil Phase is added to form an emulsion. Stop high shear agitation and switch to mixing once desired particle size is reached.
Add WPIII containing SR230 dropwisely into the emulsion under mixing at 35 C°.
Increasing temperature from 35 C.° to 75 C.° in 60 mins and hold at 75 C.° for 8 hours under mixing.

Example 22

Hybrid PU/PBAE microcapsules that encapsulate a fragrance and Captex 355 are produced in the following steps:
WPI is prepared in the same way as in Example 1. in a reactor.
WPII is prepared by mixing polyethyleneimine (PEI) in water.
Oil Phase is prepared at room temperature by mixing a fragrance, Captex 355 and Takenate D110N.
Oil Phase is then added to the WPI solution in the reactor at 1200 rpm. Start applying high shear agitation at 2000 rpm at 25 C.° after all of the Oil Phase is added to form an emulsion. Stop high shear agitation and switch to mixing once desired particle size is reached.
Add WP II containing PEI slowly into the emulsion under mixing at 25 C°.
Add WPIII containing SR415 into the above emulsion 5 minutes after the addition of WPII.
Increasing the temperature after all WPIII is added from 35 C.° to 75 C.° in 60 mins and hold at 75 C.° for 8 hours under mixing
Optionally, aluminum sulfate may be added to the above emulsion under mixing.

Example 23

Hybrid PU/PBAE microcapsules that encapsulate a fragrance and Captex 355 are produced in the following steps:
WPI is prepared in the same way as in Example 1 in a reactor.
WPII is prepared in the same way as in Example 22.
Oil Phase is prepared in the same way as in Example 22.
Oil Phase is then added to the WPI solution in the reactor at 1200 rpm. Start applying high shear agitation at 2000 rpm at 25 C.° after all of the Oil Phase is added to form an emulsion. Stop high shear agitation and switch to mixing once desired particle size is reached.
Add WPII containing PEI slowly into the emulsion under mixing at 25 C°.
Add WPIII containing SR454 into the above emulsion 5 minutes after the addition of WPII.
Increasing the temperature after all WPIII is added from 35 C.° to 75 C.° in 60 mins and hold at 75 C.° for 8 hours under mixing
Optionally, aluminum sulfate may be added to the above emulsion under mixing.

Example 24

Hybrid PU/PBAE microcapsules that encapsulate a fragrance and Captex 355 are produced in the following steps:
WPI is prepared in the same way as in Example 1 in a reactor.
WPII is prepared in the same way as in Example 22.
Oil Phase is prepared in the same way as in Example 22.
Oil Phase is then added to the WPI solution in the reactor at 1200 rpm. Start applying high shear agitation at 2000 rpm at 25 C.° after all of the Oil Phase is added to form an emulsion. Stop high shear agitation and switch to mixing once desired particle size is reached.
Add WPII containing PEI slowly into the emulsion under mixing at 25 C°.
Add WPIII containing SR230 into the above emulsion 5 minutes after the addition of WPII.
Increasing the temperature after all WPIII is added from 35 C.° to 75 C.° in 60 mins and hold at 75 C.° for 8 hours under mixing
Optionally, aluminum sulfate may be added to the above emulsion under mixing.

Example 25

Hybrid PU/PBAE microcapsules that encapsulate Nitrapyrin and Aromatic 200 are produced in the following steps:
WPI is prepared in the same way as in Example 1 in a reactor.
WPII is prepared in the same way as in Example 22.
Oil Phase is prepared at room temperature by mixing Nitrapyrin, Aromatic 200 and Takenate D110N.
Oil Phase is then added to the WPI in the reactor at 1200 rpm. Start applying high shear agitation at 2000 rpm at 25 C.° after all of the Oil Phase is added to form an emulsion. Stop high shear agitation and switch to mixing once desired particle size is reached.
Add WPII containing PEI slowly into the emulsion under mixing at 25 C°.
Add WPIII containing SR415 into the above emulsion 5 minutes after the addition of WPII.
Increasing the temperature after all WPIII is added from 35 C.° to 75 C.° in 60 mins and hold at 75 C.° for 8 hours under mixing.
Optionally, aluminum sulfate may be added to the above emulsion under mixing.

Example 26

Hybrid PU/PBAE microcapsules that encapsulate Nitrapyrin and Aromatic 200 are produced in the following steps:

WPI is prepared in the same way as in Example 1 in a reactor.

WPII is prepared in the same way as in Example 22.

Oil Phase is prepared in the same way as in Example 25.

Oil Phase is then added to the WPI solution in the reactor at 1200 rpm. Start applying high shear agitation at 2000 rpm at 25 C.° after all of the Oil Phase is added to form an emulsion. Stop high shear agitation and switch to mixing once desired particle size is reached.

Add WPII containing PEI slowly into the emulsion under mixing at 25 C°.

Add WPIII containing SR415 into the above emulsion 5 minutes after the addition of WPII.

Increasing the temperature after all WPIII is added from 35 C.° to 75 C.° in 60 mins and hold at 75 C.° for 8 hours under mixing.

Optionally, aluminum sulfate may be added to the above emulsion under mixing.

Example 27

Hybrid PU/PBAE microcapsules that encapsulate Nitrapyrin and Aromatic 200 are produced in the following steps:

WPI is prepared in the same way as in Example 1 in a reactor.

WPII is prepared in the same way as in Example 22.

Oil Phase is prepared in the same way as in Example 25.

Oil Phase is then added to the WPI solution in the reactor at 1200 rpm. Start applying high shear agitation at 2000 rpm at 25 C.° after all of the Oil Phase is added to form an emulsion. Stop high shear agitation and switch to mixing once desired particle size is reached.

Add WPII containing PEI slowly into the emulsion under mixing at 25 C°.

Add WPIII containing SR230 acrylate into the above emulsion 5 minutes after the addition of WPII.

Increasing the temperature after all WPIII is added from 35 C.° to 75 C.° in 60 mins and hold at 75 C.° for 8 hours under mixing.

Optionally, aluminum sulfate may be added to the above emulsion under mixing.

TABLE 2

| Components | Example 1 | Example 2 | Example 3 | Example 4 | Example 5 | Example 6 | Example 7 |
|---|---|---|---|---|---|---|---|
| Water phase I | | | | | | | |
| Deionized water | 55.00 | 55.00 | 85.50 | 85.50 | 85.50 | 30.84 | 66.67 |
| 5% Selvol 540 | 50.00 | 50.00 | 48.00 | 48.00 | 48.00 | 56.54 | 66.67 |
| Water phase II | | | | | | | |
| Deionized water | 87.50 | 87.50 | 46.50 | 46.50 | 46.50 | 71.96 | 116.67 |
| Diethylenetriamine | 5.40 | 5.40 | 6.48 | 6.48 | 6.48 | 5.55 | 9.00 |
| SR230 | 11.20 | 11.20 | 13.44 | 13.44 | 13.44 | 11.51 | 18.67 |
| Water phase III | | | | | | | |
| SR230 | 11.20 | 11.20 | 13.44 | 13.44 | 0.00 | 11.51 | 18.67 |
| SR351 | 0.00 | 0.00 | 0.00 | 0.00 | 13.44 | 0.00 | 0.00 |
| Oil phase | | | | | | | |
| Perfume 1 | 56.04 | 56.04 | 67.25 | 0.00 | 0.00 | 0.00 | 0.00 |
| Captex 355 | 56.04 | 56.04 | 67.25 | 0.00 | 0.00 | 0.00 | 0.00 |
| Perfume 2 | 0.00 | 0.00 | 0.00 | 114.32 | 114.32 | 0.00 | 0.00 |
| Isopropyl myristate | 0.00 | 0.00 | 0.00 | 20.17 | 20.17 | 0.00 | 0.00 |
| Nitrapyrin | 0.00 | 0.00 | 0.00 | 0.00 | 0.00 | 57.61 | 93.40 |
| Aromatic 200 | 0.00 | 0.00 | 0.00 | 0.00 | 0.00 | 57.61 | 93.40 |
| Desmodur W | 3.00 | 3.00 | 0.00 | 0.00 | 0.00 | 3.08 | 0.00 |
| Takenate D110N | 0.00 | 0.00 | 3.60 | 3.60 | 3.60 | 0.00 | 5.00 |
| Desmodur N3400 | 0.00 | 0.00 | 0.00 | 0.00 | 0.00 | 0.00 | 0.00 |
| Median particle size/micron | 13.49 | 13.01 | 10.46 | 11.81 | 20.14 | 14.87 | 20.39 |
| % Solid | 46.37 | 46.22 | 49.74 | 50.10 | 51.92 | 56.94 | 51.71 |
| % free core | 3.98 | 2.59 | 11.44 | 9.42 | — | 0.47 | 0.02 |
| 1 week leakage/% | 86.44 | 36.55 | 97.64 | — | 33.52 | — | — |
| 90 mins release/% | — | — | — | — | — | 85.77 | 0.88 |
| 28 day degradation/% | — | 42.41 | — | — | — | — | — |

TABLE 3

| Components | Example 8 | Example 9 | Example 10 | Example 11 | Example 12 | Example 13 | Example 14 |
|---|---|---|---|---|---|---|---|
| Water phase I | | | | | | | |
| Deionized water | 66.67 | 85.50 | 85.50 | 85.50 | 85.50 | 65.00 | 75.00 |
| 5% Selvol 540 | 66.67 | 48.00 | 48.00 | 48.00 | 48.00 | 50.00 | 41.00 |
| Water phase II | | | | | | | |
| Deionized water | 116.67 | 46.50 | 46.50 | 46.50 | 46.50 | 77.50 | 38.75 |
| Diethylenetriamine | 9.00 | 6.48 | 6.48 | 6.48 | 6.48 | 10.80 | 5.40 |
| SR230 | 18.67 | 13.44 | 13.44 | 13.44 | 13.44 | 22.40 | 11.20 |

TABLE 3-continued

| Components | Example 8 | Example 9 | Example 10 | Example 11 | Example 12 | Example 13 | Example 14 |
|---|---|---|---|---|---|---|---|
| Water phase III | | | | | | | |
| SR230 | 18.67 | 0.00 | 0.00 | 0.00 | 0.00 | 0.00 | 0.00 |
| SR351 | 0.00 | 16.32 | 16.32 | 16.32 | 16.32 | 30.50 | 11.90 |
| Oil phase | | | | | | | |
| Perfume | 0.00 | 67.25 | 67.25 | 67.25 | 67.25 | 56.04 | 56.04 |
| Captex 355 | 0.00 | 67.25 | 67.25 | 67.25 | 67.25 | 56.04 | 56.04 |
| Nitrapyrin | 93.40 | 0.00 | 0.00 | 0.00 | 0.00 | 0.00 | 0.00 |
| Aromatic 200 | 93.40 | 0.00 | 0.00 | 0.00 | 0.00 | 0.00 | 0.00 |
| Desmodur W | 0.00 | 3.60 | 3.60 | 3.60 | 3.60 | 1.00 | 7.00 |
| Takenate D110N | 5.00 | 0.00 | 0.00 | 0.00 | 0.00 | 0.00 | 0.00 |
| Median particle size/Micron | 12.25 | 26.31 | 27.28 | 28.99 | 33.13 | 29.35 | 27.95 |
| % Solid | 51.29 | 54.66 | 54.56 | 53.34 | 47.92 | 50.00 | 49.92 |
| % free core | 0.07 | 0.12 | 0.10 | 0.12 | 0.17 | 0.65 | 0.07 |
| 1 week leakage/% | 28.32 | 31.27 | 27.92 | 30.51 | 57.83 | 30.32 | 28.32 |
| 90 mins leakage/% | 5.38 | — | — | — | — | — | — |
| 28 day degradation/% | — | 44.35 | 14.08 | 15.68 | — | 19.78 | — |

TABLE 4

| Components | Example 15 | Example 16 | Example 17 | Example 18 | Example 19 |
|---|---|---|---|---|---|
| Water phase I | | | | | |
| Deionized water | 90.00 | 150.00 | 150.00 | 150.00 | 150.00 |
| 5% Selvol 540 | 49.20 | 57.60 | 57.60 | 57.60 | 57.60 |
| Water phase II | | | | | |
| Deionized water | 46.50 | 23.25 | 23.25 | 23.25 | 23.25 |
| Diethylenetriamine | 6.48 | 3.24 | 3.24 | 3.24 | 3.24 |
| SR230 | 13.44 | 6.72 | 6.72 | 6.72 | 6.72 |
| Oil phase | | | | | |
| Perfume | 67.25 | 99.00 | 99.00 | 99.00 | 99.00 |
| Captex 355 | 67.25 | 99.00 | 99.00 | 99.00 | 99.00 |
| Desmodur W | 24.12 | 12.06 | 12.06 | 12.06 | 12.06 |
| Median particle size/microns | 21.93 | 26.63 | 23.02 | 20.83 | 19.32 |
| % Solid | 51.57 | 50.41 | 50.73 | 49.54 | 50.05 |
| % free core | 0.01 | 0.14 | 0.13 | 0.12 | 0.17 |
| 1 week leakage/% | 22.93 | 44.11 | 32.07 | 33.43 | 42.04 |
| 28 day degradation/% | 11.81 | 19.31 | 14.69 | 21.19 | 13.79 |

TABLE 5

| Components | Example 20 | Example 21 | Example 22 | Example 23 | Example 24 | Example 25 | Example 26 | Example 27 |
|---|---|---|---|---|---|---|---|---|
| Water phase I | | | | | | | | |
| Deionized water | 55.00 | 55.00 | 219.00 | 219.00 | 219.00 | 175.20 | 156.76 | 110.00 |
| 5% Selvol 540 | 50.00 | 50.00 | 69.16 | 69.16 | 69.16 | 55.33 | 73.77 | 101.50 |
| Water phase II | | | | | | | | |
| Deionized water | 87.50 | 87.50 | 25.00 | 25.00 | 25.00 | 20.00 | 20.00 | 25.00 |
| Diethylenetriamine | 5.40 | 0.00 | 0.00 | 0.00 | 0.00 | 0.00 | 0.00 | 0.00 |
| Ethylenediamine | 0.00 | 5.40 | 0.00 | 0.00 | 0.00 | 0.00 | 0.00 | 0.00 |
| SR230 | 11.20 | 11.20 | 0.00 | 0.00 | 0.00 | 0.00 | 0.00 | 0.00 |
| Polyethyleneimine, MW 600 | 0.00 | 0.00 | 5.72 | 5.72 | 5.72 | 5.72 | 5.72 | 5.72 |
| Water phase III | | | | | | | | |
| SR230 | 11.20 | 11.20 | 0.00 | 0.00 | 22.40 | 0.00 | 0.00 | 22.40 |
| SR415 | 0.00 | 0.00 | 22.40 | 0.00 | 0.00 | 22.40 | 22.40 | 0.00 |
| SR454 | 0.00 | 0.00 | 0.00 | 22.40 | 0.00 | 0.00 | 0.00 | 0.00 |
| Oil phase | | | | | | | | |
| Perfume | 56.04 | 56.04 | 112.08 | 112.08 | 112.08 | 0.00 | 0.00 | 0.00 |
| Captex 355 | 56.04 | 56.04 | 112.08 | 112.08 | 112.08 | 0.00 | 0.00 | 0.00 |
| Nitrapyrin | 0.00 | 0.00 | 0.00 | 0.00 | 0.00 | 112.08 | 112.08 | 112.08 |

TABLE 5-continued

| Components | Example 20 | Example 21 | Example 22 | Example 23 | Example 24 | Example 25 | Example 26 | Example 27 |
|---|---|---|---|---|---|---|---|---|
| Aromatic 200 | 0.00 | 0.00 | 0.00 | 0.00 | 0.00 | 112.08 | 112.08 | 112.08 |
| Desmodur W | 0.00 | 3.00 | 0.00 | 0.00 | 0.00 | 0.00 | 0.00 | 0.00 |
| Takenate D110N | 0.00 | 0.00 | 4.00 | 4.00 | 4.00 | 2.00 | 2.00 | 2.00 |
| Desmodur N3400 | 3.00 | 0.00 | 0.00 | 0.00 | 0.00 | 0.00 | 0.00 | 0.00 |
| Median particle size/microns | 60.06 | 11.39 | 20.39 | 20.14 | 21.40 | 17.27 | 12.48 | 9.97 |
| % Solid | 45.83 | 43.84 | 44.79 | 45.38 | 41.61 | 49.34 | 48.87 | 50.23 |
| % free core | 11.27 | 11.28 | 1.13 | 0.32 | 0.42 | 0.05 | 0.04 | 0.02 |
| 1 week leakage/% | 93.43 | 93.27 | — | — | — | — | — | — |
| 90 mins leakage/% | — | — | — | — | — | 0.22 | 0.59 | 1.02 |

The invention claimed is:

1. A polyurea and poly(beta-amino esters) (PU/PBAE) microcapsule, comprising: a core material; and
a shell comprising PU, hybrid PU/PBAE, and PBAE,
wherein the PBAE comprises a reaction product of a multifunctional amine and a multifunctional acrylate having an α,β-unsaturated carbonyl, wherein the multifunctional amine adds by aza-Michael addition to a β-carbon atom of the α,β-unsaturated carbonyl.

2. The PU/PBAE microcapsule of claim 1, wherein the shell is derived from i) 5% to 90% of a preformed PBAE prepolymer, or polyamines, or a reaction product of a first multifunctional acrylate and a multifunctional amine, ii) 0.1% to 90% of a polyisocyanate, and iii) 0% to 90% of a second multifunctional acrylate, by weight of the shell.

3. The PU/PBAE microcapsule of claim 2, wherein the preformed PBAE prepolymer is derived from the first multifunctional acrylate and the multifunctional amine, wherein a molar ratio of the first multifunctional acrylate to the multifunctional amine is in a range between 100/1-1/100.

4. The PU/PBAE microcapsule of claim 3, wherein the molar ratio of the first multifunctional acrylate to the multifunctional amine is in a range between 10/1-1/10.

5. The PU/PBAE microcapsule of claim 3, wherein the molar ratio of the first multifunctional acrylate to the multifunctional amine is in a range between 2/1-1/2.

6. The PU/PBAE microcapsule of claim 2, wherein a molar ratio of the polyisocyanate to the multifunctional amine is 1/100-1/1.

7. The PU/PBAE microcapsule of claim 1, wherein the shell has a single shell structure comprising hybrid PU/PBAE.

8. The PU/PBAE microcapsule of claim 1, wherein the shell has a dual shell structure comprising an inner shell and an outer shell, a composition of the inner shell comprises hybrid PU/PBAE, a composition of the outer shell comprises PBAE, wherein the composition of the outer shell crosslinks or deposits to the composition of the inner shell.

9. The PU/PBAE microcapsule of claim 1, wherein the shell has a multi-shell structure comprising an inner shell, a transitional shell and an outer shell, a composition of the inner shell comprises PU, a composition of the transitional shell comprises hybrid PU/PBAE, a composition of the outer shell comprises PBAE, and the composition of each shell crosslinks or deposits to the composition of an adjacent shell.

10. The PU/PBAE microcapsule of claim 1, wherein a median particle size of the PU/PBAE microcapsule is 3-100 μm.

11. The PU/PBAE microcapsule of claim 1, wherein a zeta potential of the PU/PBAE microcapsule is −100 mV-+200 mV at pH 3 and −200 mV-+100 mV at pH 10.

12. A method of producing the PU/PBAE microcapsule of claim 1, comprising:
providing a first aqueous solution comprising an emulsifier and water;
providing a second aqueous solution comprising a multifunctional amine, a first multifunctional acrylate having an α,β-unsaturated carbonyl, and water, and mixing the second aqueous solution at a first temperature for a first period of time to form a PBAE prepolymer, wherein the PBAE prepolymer is a reaction product of the multifunctional amine and the first multifunctional acrylate having an α,β-unsaturated carbonyl, wherein the multifunctional amine adds by aza-Michael addition to a β-carbon atom of the α,β-unsaturated carbonyl;
adding the first aqueous solution into the second aqueous solution under mixing to obtain a mixture of the first aqueous solution and the second aqueous solution;
providing an oil phase comprising the core material and a polyisocyanate;
adding the oil phase into the mixture of the first aqueous solution and the second aqueous solution, applying high shear agitation until a target particle size is reached to obtain an emulsion at a second temperature;
providing a third aqueous solution comprising a second multifunctional acrylate, adding the third aqueous solution into the emulsion under mixing; and
increasing a temperature to a third temperature in a second period of time and holding the temperature at the third temperature for a third period of time under mixing.

13. The method of claim 12, the multifunctional amine is diethylenetriamine, ethylenediamine, tetraethylenepentaamine, pentaethylenehexamine or polyethylenimine, the first and the second multifunctional acrylate is diethylene glycol diacrylate, triethylene glycol diacrylate, tetraethylene glycol diacrylate, poly(ethylene glycol) diacrylate, trifunctional trimethylolpropane triacrylate, ethoxylated trimethylolpropane triacrylate or a combination thereof independently, and the polyisocyanate is dicyclohexylmethane diisocyanate, hexamethylene diisocyanate uretdione, or xylene diisocyanate based aliphatic polyisocyanate adduct prepolymer.

14. The method of claim 12, wherein the first temperature is 25-70° C., the second temperature is 5-55° C., the third temperature is 50-95° C., the first period of time is 10-360 mins, the second period of time is 30-120 mins, and the third period of time is 2-24 hours.

15. A method of producing the PU/PBAE microcapsule of claim 1, comprising:
providing a first aqueous solution comprising an emulsifier and water;

providing a second aqueous solution comprising a multifunctional amine and water;

adding the first aqueous solution into the second aqueous solution under mixing to obtain a mixture of the first aqueous solution and the second aqueous solution;

providing an oil phase comprising the core material and a polyisocyanate;

adding the oil phase into the mixture of the first aqueous solution and the second aqueous solution, applying high shear agitation at a first temperature until a target particle size is reached to obtain an emulsion;

providing a third aqueous solution comprising a multifunctional acrylate having an α,β-unsaturated carbonyl, adding the third aqueous solution into the emulsion under mixing, wherein the multifunctional amine reacts with the multifunctional acrylate having the α,β-unsaturated carbonyl to form PBAE, in which the multifunctional amine adds by aza-Michael addition to a β-carbon atom of the α,β-unsaturated carbonyl; and increasing a temperature to a second temperature in a first period of time and holding the temperature at the second temperature for a second period of time under mixing.

16. The method of claim 15, the multifunctional amine is diethylenetriamine, ethylenediamine, tetraethylenepentaamine, tentaethylenehexamine or olyethylenimine, the multifunctional acrylate is diethylene glycol diacrylate, triethylene glycol diacrylate, tetraethylene glycol diacrylate, poly(ethylene glycol) diacrylate, trifunctional trimethylolpropane triacrylate, ethoxylated trimethylolpropane triacrylate, or a combination thereof, and the polyisocyanate is dicyclohexylmethane diisocyanate, hexamethylene diisocyanate uretdione, or a xylyene diisocyanate (XDI) based aliphatic polyisocyanate adduct prepolymer.

17. The method of claim 15, wherein the first temperature is 5-55° C., the second temperature is 50-95° C., the first period of time is 30-120 mins, the second period of time is 2-24 hours.

18. A method of producing the PU/PBAE microcapsule of claim 1, comprising:

providing a first aqueous solution comprising an emulsifier and water;

providing a second aqueous solution comprising a multifunctional amine, a multifunctional acrylate having an α,β-unsaturated carbonyl, and water, and mixing the second aqueous solution at a first temperature for a first period of time to form a PBAE prepolymer, wherein the PBAE prepolymer is a reaction product of the multifunctional amine and the multifunctional acrylate having the α,β-unsaturated carbonyl, wherein the multifunctional amine adds by aza-Michael addition to a β-carbon atom of the α,β-unsaturated carbonyl;

adding the first aqueous solution into the second aqueous solution under mixing to obtain a mixture of the first aqueous solution and the second aqueous solution;

providing an oil phase comprising the core material and a polyisocyanate;

adding the oil phase into the mixture of the first aqueous solution and the second aqueous solution, applying high shear agitation at a second temperature until a target particle size is reached to obtain an emulsion; and increasing a temperature to a third temperature in a second period of time and holding the temperature at the third temperature for a third period of time under mixing.

19. The method of claim 18, the multifunctional amine is diethylenetriamine, ethylenediamine, tetraethylenepentaamine, pentaethylenehexamine or polyethylenimine, the multifunctional acrylate is diethylene glycol diacrylate, triethylene glycol diacrylate, tetraethylene glycol diacrylate, poly(ethylene glycol) diacrylate, trifunctional trimethylolpropane triacrylate, ethoxylated trimethylolpropane triacrylate, or a combination thereof, and the polyisocyanate is dicyclohexylmethane diisocyanate, hexamethylene diisocyanate uretdione, or xylyene diisocyanate (XDI) based aliphatic polyisocyanate adduct prepolymer.

20. The method of claim 18, wherein the first temperature is 25-70° C., the second temperature is 5-55° C., the third temperature is 50-95° C., the first period of time is 10-360 mins, the second period of time is 30-120 mins, and the third period of time is 2-24 hours.

21. A method of producing the PU/PBAE microcapsule of claim 1, comprising:

providing a first aqueous solution comprising an emulsifier and water;

providing a second aqueous solution comprising a multifunctional amine, a first multifunctional acrylate having an α,β-unsaturated carbonyl, and water, and mixing the second aqueous solution at a first temperature for a first period of time to form a PBAE prepolymer, wherein the PBAE prepolymer is a reaction product of the multifunctional amine and the first multifunctional acrylate having the α,β-unsaturated carbonyl, wherein the multifunctional amine adds by aza-Michael addition to a β-carbon atom of the α,β-unsaturated carbonyl;

providing an oil phase comprising the core material and a polyisocyanate;

adding the oil phase into the first aqueous solution, applying high shear agitation at a second temperature until a target particle size is reached to obtain a first emulsion;

adding the second aqueous solution into the first emulsion under mixing to obtain a second emulsion;

providing a third aqueous solution comprising a second multifunctional acrylate, and adding the third aqueous solution into the second emulsion under mixing; and increasing a temperature to a third temperature in a second period of time and hold the temperature at the third temperature for a third period of time under mixing.

22. The method of claim 21, the multifunctional amine is diethylenetriamine, ethylenediamine, tetraethylenepentaamine, pentaethylenehexamine or polyethylenimine, the first and the second multifunctional acrylate is diethylene glycol diacrylate, triethylene glycol diacrylate, tetraethylene glycol diacrylate, poly(ethyl ene glycol) diacrylate, trifunctional trimethylolpropane triacrylate, ethoxylated trimethylolpropane triacrylate, or a combination thereof independently, and the polyisocyanate is dicyclohexylmethane diisocyanate, hexamethylene diisocyanate uretdione, or xylyene diisocyanate (XDI) based aliphatic polyisocyanate adduct prepolymer.

23. The method of claim 21, wherein the first temperature is 25-70° C., the second temperature is 5-55° C., the third temperature is 50-95° C., the first period of time is 10-360 mins, the second period of time is 30-120 mins, and the third period of time is 2-24 hours.

24. A method of producing the PU/PBAE microcapsule of claim 1, comprising:

providing a first aqueous solution comprising an emulsifier and water;

providing a second aqueous solution comprising a multifunctional amine and water;

providing an oil phase comprising the core material and a polyisocyanate;

adding the oil phase into the first aqueous solution, applying high shear agitation at a first temperature until a target particle size is reached to obtain a first emulsion;

adding the second aqueous solution into the first emulsion under mixing to obtain a second emulsion;

providing a third aqueous solution comprising a multifunctional acrylate having an α,β-unsaturated carbonyl, and adding the third aqueous solution into the second emulsion under mixing, wherein the multifunctional amine reacts with the multifunctional acrylate having the α,β-unsaturated carbonyl to form PBAE, in which the multifunctional amine adds by aza-Michael addition to a β-carbon atom of the α,β-unsaturated carbonyl; and increasing a temperature to a second temperature in a first period of time and hold the temperature at the second temperature for a second period of time under mixing.

25. The method of claim 24, the multifunctional amine is diethylenetriamine, ethylenediamine, tetraethylenepentaamine, pentaethylenehexamine or polyethylenimine, the multifunctional acrylate is diethylene glycol diacrylate, triethylene glycol diacrylate, tetraethylene glycol diacrylate, poly(ethylene glycol) diacrylate, trifunctional trimethylolpropane triacrylate, ethoxylated trimethylolpropane triacrylate, or a combination thereof, and the polyisocyanate is dicyclohexylmethane diisocyanate, hexamethylene diisocyanate uretdione, or xylyene diisocyanate (XDI) based aliphatic polyisocyanate adduct prepolymer.

26. The method of claim 24, wherein the first temperature is 5-55° C., the second temperature is 50-95° C., the first period of time is 30-120 mins, the second period of time is 2-24 hours.

27. A method of producing the PU/PBAE microcapsule of claim 1, comprising:

providing a first aqueous solution comprising an emulsifier and water;

providing a second aqueous solution comprising a multifunctional amine, a multifunctional acrylate having an α,β-unsaturated carbonyl, and water, and mixing the second aqueous solution at a first temperature for a first period of time to form a PBAE prepolymer, wherein the PBAE prepolymer is a reaction product of the multifunctional amine and the multifunctional acrylate having the α,β-unsaturated carbonyl, wherein the multifunctional amine adds by aza-Michael addition to a β-carbon atom of the α,β-unsaturated carbonyl;

providing an oil phase comprising the core material and a polyisocyanate;

adding the oil phase into the first aqueous solution, applying high shear agitation at a second temperature until a target particle size is reached to obtain a first emulsion;

adding the second aqueous solution into the first emulsion under mixing to obtain a second emulsion; and increasing a temperature to a third temperature in a second period of time and hold the temperature at the third temperature for a third period of time under mixing.

28. The method of claim 27, the multifunctional amine is diethylenetriamine, ethylenediamine, tetraethylenepentaamine, pentaethylenehexamine or polyethylenimine, the multifunctional acrylate is diethylene glycol diacrylate, triethylene glycol diacrylate, tetraethylene glycol diacrylate, poly(ethylene glycol) diacrylate, trifunctional trimethylolpropane triacrylate, ethoxylated trimethylolpropane triacrylate, or a combination thereof, and the polyisocyanate is dicyclohexylmethane diisocyanate, hexamethylene diisocyanate uretdione, or xylyene diisocyanate (XDI) based aliphatic polyisocyanate adduct prepolymer.

29. The method of claim 27, wherein the first temperature is 25-70° C., the second temperature is 5-55° C., the third temperature is 50-95° C., the first period of time is 10-360 mins, the second period of time is 30-120 mins, and the third period of time is 2-24 hours.

30. An article of manufacture incorporating the PU/PBAE microcapsule according to claim 1.

31. The article of manufacture according to claim 30, wherein the article is a soap, a surface cleaner, a laundry detergent, a fabric softener, a shampoo, a textile, a paper towel, an adhesive, a wipe, a diaper, a feminine hygiene product, a facial tissue, a pharmaceutical, a napkin, a deodorant, a heat sink, a foam, a pillow, a mattress, bedding, a cushion, a cosmetic, a medical device, packaging, an agricultural product, a cooling fluid, a wallboard, or an insulation.

* * * * *